(12) United States Patent
Kato et al.

(10) Patent No.: US 6,623,618 B1
(45) Date of Patent: Sep. 23, 2003

(54) GAS SENSOR AND METHOD FOR CONTROLLING THE SAME

(75) Inventors: Nobuhide Kato, Ama-gun (JP); Yasuhiko Hamada, Nagoya (JP); Nobuyuki Kokune, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 394 days.

(21) Appl. No.: 09/598,811

(22) Filed: Jun. 21, 2000

Related U.S. Application Data

(63) Continuation-in-part of application No. 09/213,981, filed on Dec. 17, 1998, now abandoned.

(30) Foreign Application Priority Data

Dec. 22, 1997 (JP) .............................................. 9-353304

(51) Int. Cl.[7] .......................................... G01N 27/407
(52) U.S. Cl. ..................... 205/781; 205/784; 204/425; 204/426; 204/427; 204/73; 204/23.31
(58) Field of Search ................. 205/781, 784, 205/784.5; 204/425, 426, 427; 73/23.31, 23.32

(56) References Cited

U.S. PATENT DOCUMENTS

| | | |
|---|---|---|
| 4,042,465 A | 8/1977 | Morong, III et al. |
| 4,105,523 A | 8/1978 | Stolarczyk |
| 4,121,548 A * | 10/1978 | Hattori et al. ............... 123/479 |
| 4,272,331 A | 6/1981 | Hetrick |
| 4,384,935 A | 5/1983 | De Jong |
| 4,499,880 A | 2/1985 | Miki et al. |
| 4,622,125 A | 11/1986 | Oyama et al. |
| 4,751,907 A | 6/1988 | Yamamoto et al. |
| 4,882,030 A | 11/1989 | Suzuki et al. |
| 5,173,167 A | 12/1992 | Murase et al. |
| 5,632,883 A | 5/1997 | Hoetzel |
| 5,672,811 A | 9/1997 | Kato et al. |
| 5,763,763 A | 6/1998 | Kato et al. |
| 6,290,829 B1 * | 9/2001 | Kato et al. .................. 204/425 |

FOREIGN PATENT DOCUMENTS

| | | |
|---|---|---|
| DE | 196 10 911 A1 | 9/1997 |
| EP | 0 427 958 A1 | 5/1991 |
| EP | 0 769 693 | 4/1997 |
| EP | 0 807 818 | 11/1997 |
| JP | 8-271476 | 10/1996 |
| JP | 9-113484 | 5/1997 |
| WO | 00/10001 | 2/2000 |

OTHER PUBLICATIONS

Patent Abstracts of Japan, vol. 008, No. 058 (P–261), Mar. 16, 1984 & JP 58–205849 A (Toyota Jidosha Kogyo KK), Nov. 30, 1983.

* cited by examiner

*Primary Examiner*—Nam Nguyen
*Assistant Examiner*—Kaj K. Olsen
(74) *Attorney, Agent, or Firm*—Burr & Brown

(57) ABSTRACT

Disclosed is a gas sensor for controlling a concentration of oxygen and/or measuring NOx by allowing a current to flow through an ion-conductive member for conducting oxygen ion, by the aid of a current supply circuit, wherein the current, which is outputted from the current supply circuit, has a pulse waveform (current signal) having a constant crest value, and the current supply circuit comprises a rectangular wave-generating circuit for controlling a frequency of the current signal on the basis of an electromotive force generated in the ion-conductive member to which the current signal is supplied. Accordingly, it is possible to highly accurately measure the predetermined gas component while scarcely being affected by the electric noise or the like.

6 Claims, 17 Drawing Sheets

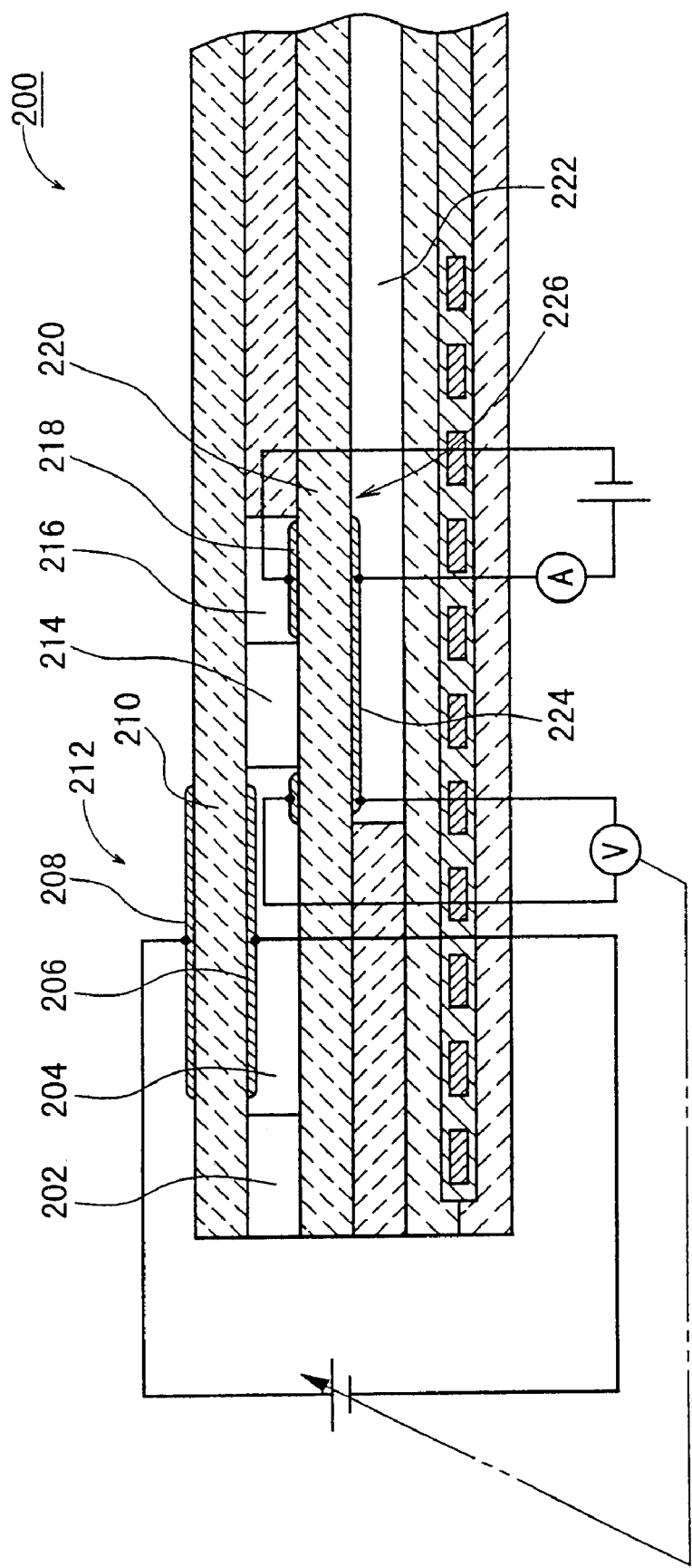
FIG. 15 - PRIOR ART

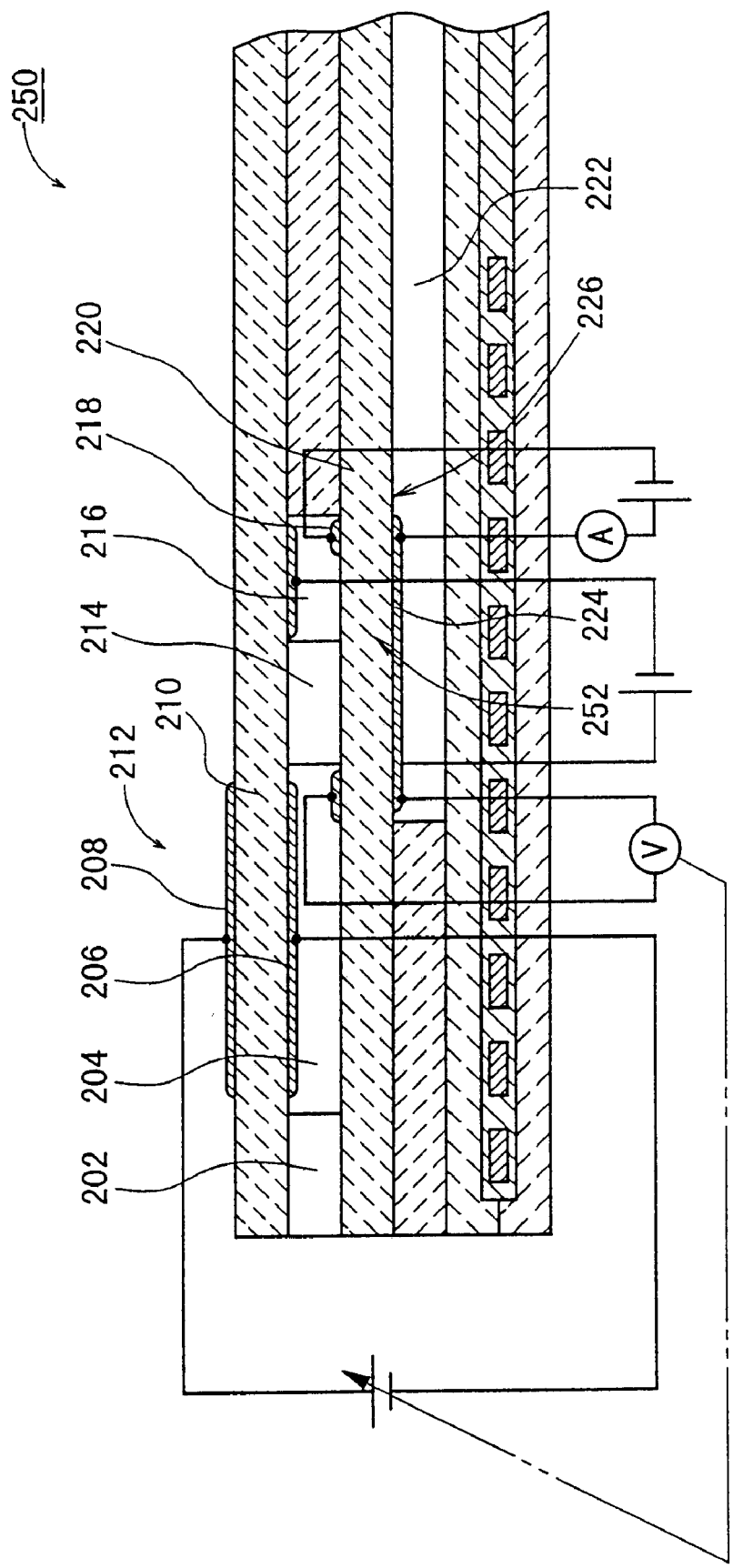
FIG. 16 - PRIOR ART

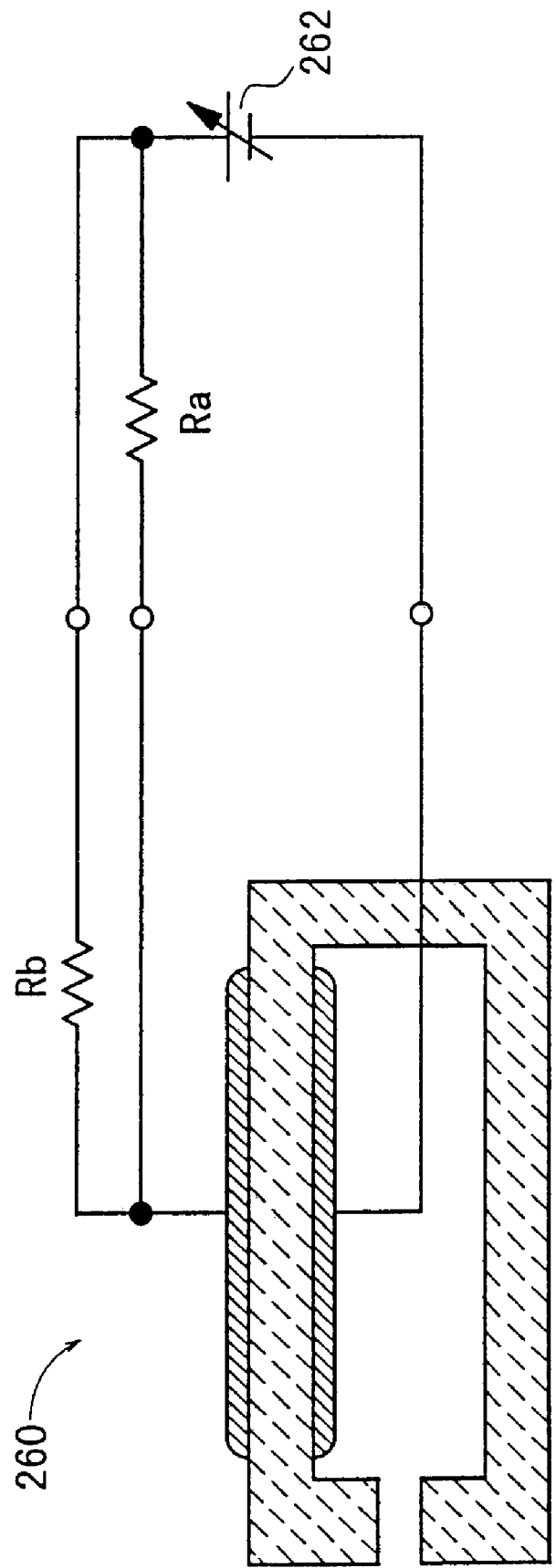
FIG. 17 - PRIOR ART

GAS SENSOR AND METHOD FOR CONTROLLING THE SAME

CROSS REFERENCE TO RELATED APPLICATION

This is a continuation-in-part application of U.S. Ser. No. 09/213,981 now abandoned, filed Dec. 17, 1998, the entirety of which is incorporated herein by reference.

BACKGROUND OF THE INVENTION

1. Field of the Invention

The present invention relates to a gas sensor and a method for controlling the same for measuring oxides such as NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Recently, an oxygen sensor is widely known, for measuring a specified gas component, for example, oxygen, in which the voltage or the current is controlled to apply it to an oxygen pump based on the use of an oxygen ion-conductive member composed of a solid electrolyte of $ZrO_2$ so that oxygen is pumped in or pumped out under a predetermined diffusion resistance to measure a limiting current obtained during this process (see, for example, Japanese Laid-Open Patent Publication No. 8-271476).

Another sensor is also known, in which a proton pump is constructed by using an oxygen-proton ion-conductive member so that the limiting current is measured on the basis of the same principle as that used in the oxygen sensor to measure $H_2$ and $H_2O$.

A NOx sensor 200 as shown in FIG. 15 is also known, which is used to measure, for example, NOx as a specified gas component.

The NOx sensor 200 is operated as follows. That is, a measurement gas is introduced into a first hollow space 204 via a first diffusion rate-determining section 202. A first oxygen-pumping means 212, which is constructed by an inner pumping electrode 206, an oxygen ion-conductive member 210, and an outer pumping electrode 208, is used to pump out or pump in oxygen contained in the measurement gas in such a degree that the measurement gas is not decomposed. Subsequently, the measurement gas is introduced into a second hollow space 216 via a second diffusion rate-determining section 214. A second oxygen-pumping means 226, which is constructed by a measurement gas-decomposing electrode 218 arranged in the second hollow space 216, an oxygen ion-conductive member 220, and a reference electrode 224 arranged in a reference air section 222, is used to pump out oxygen which is produced by decomposition effected by the catalytic action of the measurement gas-decomposing electrode 218. The sensor measures the value of current which is required to pump out the oxygen.

In other words, the foregoing gas sensors are operated such that the specified gas component is detected by using the ionic current, and the concentration of the predetermined gas is ensured in the internal space of the sensor by controlling the ionic current value.

However, the gas sensors as described above are disadvantageous as follows. That is, when the concentration of the measurement gas is low, the pumping current is decreased. As a result, it is difficult to perform the detection in some cases, and the accuracy is greatly deteriorated by the external electric noise in other cases.

For example, in the case of the NOx sensor 200 shown in FIG. 15, when the NOx concentration in the measurement gas is 10 ppm, the signal level is in a degree of about 0.05 $\mu A$. As a result, it is difficult to perform the detection. Further, it is feared that the measurement accuracy is greatly deteriorated due to the external electric noise.

In order to accurately control the oxygen concentration in the second hollow space 216, the present applicant has suggested a NOx sensor 250 as shown in FIG. 16. The NOx sensor 250 comprises an auxiliary pump 252 which is provided for the second hollow space 216. The controlled oxygen concentration in the first hollow space 204 is corrected so that the current, which flows through the auxiliary pump 252, is constant (see, for example, Japanese Laid-Open Patent Publication No. 9-113484 and European Patent Publication No. 0 807 818 A2).

In the case of the NOx sensor 250, the auxiliary pumping current is not more than several $\mu A$ which is small. Therefore, it has been revealed that the controlled oxygen concentration in the second hollow space 216 cannot be corrected at the desire of a user in some cases.

On the other hand, in the case of the sensors as described above, the limiting current is utilized to control the concentration of the gas component and measure the concentration thereof. Therefore, if the limiting current value is changed, the output is changed. In this context, for example, the limiting current value involves dispersion among individual sensors. At present, in order to correct the dispersion among individual sensors, a shunt resistor is provided, or a voltage divider resistor is provided.

FIG. 17 shows an arrangement of such a countermeasure. When the current, which flows to an oxygen pump 260, is detected by using a current-detecting resistor Ra, the current supply from a variable power source 262 to the oxygen pump 260 is shunted by the aid of an adjusting resistor Rb (shunt resistor).

For example, when the gas sensor has a large limiting current, the shunt resistor Rb is decreased so that the amount of shunt is increased. Thus, the amount of current, which is detected by the current-detecting resistor Ra, is decreased to be a predetermined value. On the contrary, when the gas sensor has a small limiting current, the amount of shunt is decreased so that the current, which is detected by the current-detecting resistor Ra, is adjusted to be the predetermined value.

Another method is also available such that the voltage, which is generated between the both terminals of the current-detecting resistor Ra, is subjected to voltage division by using a voltage divider circuit to obtain a predetermined output voltage.

However, when the foregoing methods (the shunt resistor system and the voltage divider resistor system) are adopted, one extra lead wire is required, in accordance with which it is necessary to use a multiple terminal connector system for connecting the control circuit and the sensor, resulting in a problem concerning the cost.

SUMMARY OF THE INVENTION

The present invention has been made considering the problems as described above, an object of which is to provide a gas sensor and a method for controlling the gas sensor which make it possible to highly accurately measure a predetermined gas component while scarcely being affected by the electric noise or the like.

Another object of the present invention is to provide a gas sensor and a method for controlling the gas sensor which are advantageous in view of the production cost and which make it possible to compensate the dispersion among individual sensors without increasing the number of terminals, in addition to the requirement described above.

A gas sensor according to the present invention comprising:
- a main pumping means for pumping-processing oxygen contained in a measurement gas introduced from external space, comprising solid electrolyte contacting with said external space, and an inner pumping electrode and an outer pumping electrode formed on inner and outer surfaces of said solid electrolyte; and
- a measuring pumping means for decomposing a predetermined gas component contained in said measurement gas after being pumping-processed by said main pumping means by the aid of a catalytic action and/or electrolysis, and pumping-processing oxygen produced by said decomposition via said outer pumping electrode of said main pumping means, wherein:
  - a concentration of oxygen is controlled and/or the predetermined gas component is measured by allowing a pulse-shaped current to flow through said measuring pumping means;
  - the gas sensor further comprising:
    - a electromotive force-measuring circuit for constantly measuring the electromotive force corresponding to a difference between an amount of oxygen produced by said decomposition of said predetermined gas component and an amount of oxygen contained in a reference gas;
    - a frequency control means for controlling a frequency of said pulse-shaped current corresponding to a difference between an the electromotive force measured by said electromotive force-measuring circuit and a comparing voltage; and
    - a measuring circuit for at least converting the frequency of the pulse-shaped current into a concentration of said predetermined gas component.

Accordingly, the concentration of oxygen is controlled and/or the predetermined gas component is measured by supplying the current from the current supply means to the measuring pumping means.

Usually, the following method is adopted in relation to the measurement of the predetermined gas component. That is, a constant voltage is applied to the measuring pumping means to measure the predetermined gas component by detecting the value of current flowing through the measuring pumping means depending on the amount of oxygen during this process. In such an ordinary method, the detected current value is extremely small. Therefore, a problem arises in that the measurement tends to be affected by the external electric noise.

On the contrary, according to the present invention, the current, which is supplied to the measuring pumping means, has the pulse waveform having the constant crest value. Further, the frequency of the pulse waveform is controlled. In such a procedure, the use of the pulse waveform makes it possible to obtain the crest value which is higher than those obtained when the current is supplied in the direct current form. Therefore, it is possible to allow the system to be scarcely affected by the electric noise or the like. The use of the frequency as the measured value makes it possible to increase the output dynamic range (frequency region) with respect to the inputted electromotive force. Thus, it is also possible to improve the measurement sensitivity.

It is preferable for the gas sensor constructed as described above that a power source for the current supply means is a constant voltage power source, and a resistor is connected in series to a current supply line to the measuring pumping means. In this arrangement, the voltage from the constant voltage power source is allowed to have a pulse-shaped voltage waveform by the aid of the current supply means. The current, which is supplied to the measuring pumping means, is a pulse-shaped current which has a crest value obtained by dividing the crest value of the voltage by the resistance value of the series resistor. In other words, the crest value of the pulse-shaped current supplied to the measuring pumping means can be adjusted by changing the resistance value of the series resistor. In this arrangement, it is preferable that the series resistor is selected or adjusted depending on performance of a sensor element.

Accordingly, it is possible to compensate the dispersion (the dispersion concerning the crest value and the output) among the individual sensors without increasing the number of terminals, which is advantageous in view of the production cost.

The gas sensor according to the present invention is preferably used for a NOx sensor for measuring NOx in a measurement gas.

In another aspect, a gas sensor according to the present invention comprising:
- a electromotive force-measuring circuit for constantly measuring the electromotive force corresponding to a difference between an amount of oxygen produced by said decomposition of said predetermined gas component and an amount of oxygen contained in a reference gas;
- a duty ratio control means for controlling a duty ratio of said pulse-shaped current corresponding to a difference between an the electromotive force measured by said electromotive force-measuring circuit and a comparing voltage; and
- a measuring circuit for at least converting the duty ratio of the pulse-shaped current into a concentration of said predetermined gas component.

According to the present invention, the current, which is supplied to the measuring pumping means, has the pulse waveform having the constant crest value. Further, the duty ratio of the pulse waveform is controlled. Also in this aspect, the use of the pulse waveform makes it possible to obtain the crest value which is higher than those obtained when the current is supplied in the direct current form. Therefore, it is possible to allow the system to be scarcely affected by the electric noise or the like. The use of the pulse width of each waveform as the measured value makes it possible to increase the output dynamic range with respect to the inputted electromotive force. Thus, it is also possible to improve the measurement sensitivity.

It is preferable for the gas sensor constructed as described above that a power source for the current supply means is a constant voltage power source, and a resistor is connected in series to a current supply line to the measuring pumping means. In this arrangement, it is preferable that the series resistor is selected or adjusted depending on performance of a sensor element. Accordingly, it is possible to compensate the dispersion among the individual sensors without increasing the number of terminals, which is advantageous in view of the production cost.

The gas sensor according to the present invention is also preferably used for a NOx sensor for measuring NOx in a measurement gas.

In still another aspect, a gas sensor according to the present invention comprising:
- a electromotive force-measuring circuit for constantly measuring the electromotive force corresponding to a difference between an amount of oxygen produced by said decomposition of said predetermined gas component and an amount of oxygen contained in a reference gas;

a crest value control means for controlling a crest value of said pulse-shaped current corresponding to a difference between an the electromotive force measured by said electromotive force-measuring circuit and a comparing voltage; and a measuring circuit for at least converting the crest value of the pulse-shaped current into a concentration of said predetermined gas component.

According to the present invention, the current, which is supplied to the measuring pumping means, has the pulse waveform. Further, the crest value of the pulse waveform is controlled. Also in this aspect, it is possible to obtain the crest value which is higher than those obtained when the current is supplied in the direct current form. Therefore, it is possible to allow the system to be scarcely affected by the electric noise or the like. As a result, it is possible to increase the output dynamic range with respect to the inputted electromotive force. Thus, it is also possible to improve the measurement sensitivity. When the crest value is detected, it is also preferable that the current having the pulse waveform is converted into a voltage to perform the detection.

It is preferable for the gas sensor constructed as described above that a resistor is connected in series to a current supply line to the measuring pumping means. In this embodiment, it is preferable that the series resistor is selected or adjusted depending on performance of a sensor element. Accordingly, it is possible to compensate the dispersion among the individual sensors without increasing the number of terminals, which is advantageous in view of the production cost. The gas sensor according to the present invention is also preferably used for a NOx sensor for measuring NOx in a measurement gas.

In still another aspect, A method for controlling a gas sensor according to the present invention, the gas sensor comprising:

a main pumping means for pumping-processing oxygen contained in a measurement gas introduced from external space, comprising solid electrolyte contacting with said external space, and an inner pumping electrode and an outer pumping electrode formed on inner and outer surfaces of said solid electrolyte; and a measuring pumping means for decomposing a predetermined gas component contained in said measurement gas after being pumping-processed by said main pumping means by the aid of a catalytic action and/or electrolysis, and pumping-processing oxygen produced by said decomposition via said outer pumping electrode of said main pumping means;

wherein a concentration of oxygen is controlled and/or the predetermined gas component is measured by allowing a pulse-shaped current to flow through said measuring pumping means;

wherein the method for controlling the gas sensor comprises the steps of:

measuring constantly the electromotive force corresponding to a difference between an amount of oxygen produced by said decomposition of said predetermined gas component and an amount of oxygen contained in a reference gas;

controlling a frequency of said pulse-shaped current corresponding to a difference between an the electromotive force measured by said electromotive force-measuring circuit and a comparing voltage; and converting at least the frequency of the pulse-shaped current into a concentration of said predetermined gas component.

In still another aspect, the present invention lies in a method for controlling a gas sensor as described above, comprises the steps of:

measuring constantly the electromotive force corresponding to a difference between an amount of oxygen produced by said decomposition of said predetermined gas component and an amount of oxygen contained in a reference gas;

controlling a duty ratio of said pulse-shaped current corresponding to a difference between an the electromotive force measured by said electromotive force-measuring circuit and a comparing voltage; and converting at least the duty ratio of the pulse-shaped current into a concentration of said predetermined gas component.

In still another aspect, the present invention lies in a method for controlling a gas sensor as described above, comprises the steps of:

measuring constantly the electromotive force corresponding to a difference between an amount of oxygen produced by said decomposition of said predetermined gas component and an amount of oxygen contained in a reference gas;

controlling a crest value of said pulse-shaped current corresponding to a difference between an the electromotive force measured by said electromotive force-measuring circuit and a comparing voltage; and converting at least the crest value of the pulse-shaped current into a concentration of said predetermined gas component.

According to the methods for controlling the gas sensors concerning the inventions described above, it is possible to allow the system to be scarcely affected by the electric noise or the like. Thus, it is possible to measure the predetermined gas component highly accurately. Further, it is possible to compensate the dispersion among the individual sensors without increasing the number of terminals, which is advantageous in view of the production cost.

The methods for controlling the gas sensors described above are preferably applicable to a NOx sensor for measuring NOx in a measurement gas.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 15 shows a sectional view illustrating a structure of an illustrative conventional gas sensor;

FIG. 16 shows a sectional view illustrating a structure of an illustrative suggested gas sensor; and FIG. 17 illustrates an arrangement of a conventional shunt resistor system.

DETAILED DESCRIPTION OF THE INVENTION

Explanation will be made below with reference to FIGS. 1 to 14 for several illustrative embodiments in which the gas sensor and the method for controlling the same according to the present invention are applied to gas sensors for measuring oxides such as NO, $NO_2$, $SO_2$, $CO_2$, and $H_2O$ contained in, for example, atmospheric air and exhaust gas discharged from vehicles or automobiles and inflammable gases such as CO and CnHm.

Figure 1:
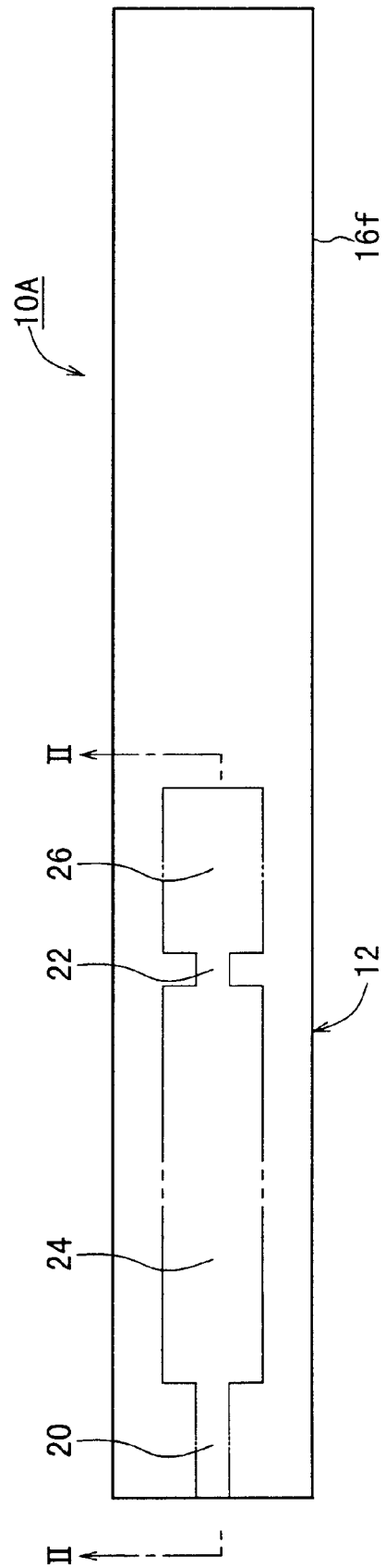
FIG. 1 shows a plan view illustrating a structure of a gas sensor according to a first embodiment.
Figure 2:
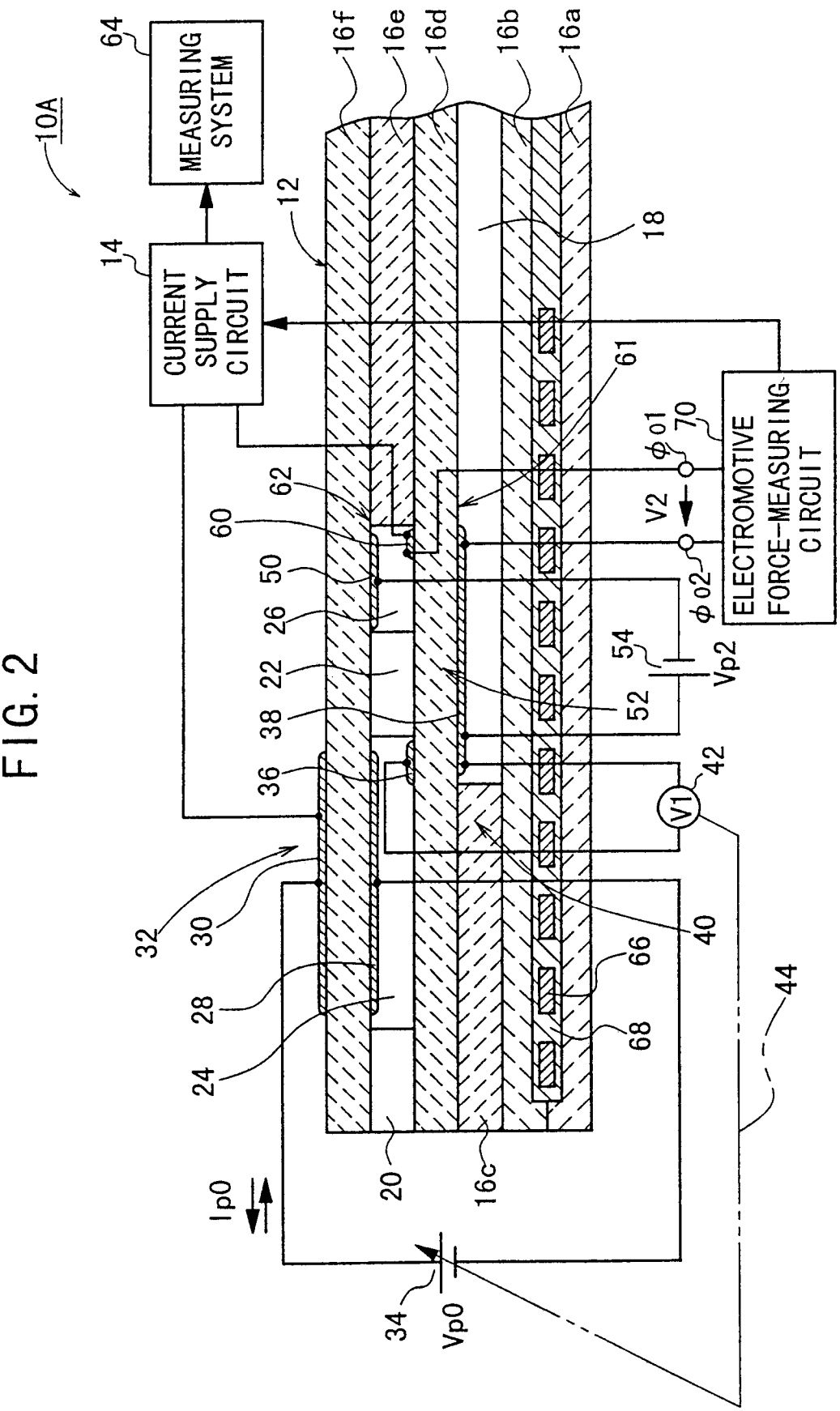
FIG. 2 shows a sectional view (a sectional view taken along a line II—II shown in FIG. 1) illustrating the structure of the gas sensor according to the first embodiment.

At first, as shown in FIGS. 1 and 2, a gas sensor 10A according to a first embodiment comprises a main sensor device 12 which is constructed to have a lengthy plate-shaped configuration as a whole, and a current supply circuit 14 for supplying a pulse-shaped current signal to the main sensor device 12.

The main sensor device 12 comprises, for example, six stacked solid electrolyte layers 16a to 16f composed of ceramics based on the use of oxygen ion-conductive solid electrolytes such as $ZrO_2$. First and second layers from the bottom are designated as first and second substrate layers 16a, 16b respectively. Third and fifth layers from the bottom are designated as first and second spacer layers 16c, 16e respectively. Fourth and sixth layers from the bottom are designated as first and second solid electrolyte layers 16d, 16f respectively.

A space (reference gas-introducing space) 18, into which a reference gas such as atmospheric air to be used as a reference for measuring oxides is introduced, is formed between the second substrate layer 16b and the first solid electrolyte layer 16d, the space 18 being comparted by a lower surface of the first solid electrolyte layer 16d, an upper surface of the second substrate layer 16b, and side surfaces of the first spacer layer 16c.

The second spacer layer 16e is interposed between the first and second solid electrolyte layers 16d, 16f. First and second diffusion rate-determining sections 20, 22 are also interposed between the first and second solid electrolyte layers 16d, 16f.

A first chamber 24 for adjusting the partial pressure of oxygen in a measurement gas is formed and comparted by a lower surface of the second solid electrolyte layer 16f, side surfaces of the first and second diffusion rate-determining sections 20, 22, and an upper surface of the first solid electrolyte layer 16d. A second chamber 26 for finely adjusting the partial pressure of oxygen in the measurement gas and measuring oxides such as nitrogen oxides (NOx) in the measurement gas is formed and comparted by a lower surface of the second solid electrolyte layer 16f, a side surface of the second diffusion rate-determining section 22, a side surface of the second spacer layer 16e, and an upper surface of the first solid electrolyte layer 16d.

The external space communicates with the first chamber 24 via the first diffusion-rate determining section 20, and the first chamber 24 communicates with the second chamber 26 via the second diffusion rate-determining section 22.

The first and second diffusion-rate determining sections 20, 22 give predetermined diffusion resistances to the measurement gas to be introduced into the first and second chambers 24, 26 respectively. Each of the first and second diffusion-rate determining sections 20, 22 can be formed as a passage composed of, for example, a porous material (for example, a porous member composed of $ZrO_2$), or a small hole having a predetermined cross-sectional area so that the measurement gas may be introduced. Alternatively, each of the first and second diffusion-rate determining sections 20, 22 may be constructed by a gap layer or a porous layer produced by printing. In this embodiment, the comparative magnitude does not matter between the respective diffusion resistances of the first and second diffusion rate-determining sections 20, 22. However, it is preferable that the diffusion resistance of the second diffusion rate-determining section 22 is larger than that of the first diffusion rate-determining section 20.

The atmosphere in the first chamber 24 is introduced into the second chamber 26 under the predetermined diffusion resistance via the second diffusion rate-determining section 22.

An inner pumping electrode 28 having a substantially rectangular planar configuration and composed of a porous cermet electrode is formed on an entire lower surface portion for forming the first chamber 24, of the lower surface of the second solid electrolyte layer 16f. An outer pumping electrode 30 is formed on a portion corresponding to the inner pumping electrode 28, of the upper surface of the second solid electrolyte layer 16f. An electrochemical pumping cell, i.e., a main pumping cell 32 is constructed by the inner pumping electrode 28, the outer pumping electrode 30, and the second solid electrolyte layer 16f interposed between the both electrodes 28, 30.

A desired control voltage (pumping voltage) Vp0 is applied between the inner pumping electrode 28 and the outer pumping electrode 30 of the main pumping cell 32 by the aid of an external variable power source 34 to allow a pumping current Ip0 to flow in a positive direction or in a negative direction between the outer pumping electrode 30 and the inner pumping electrode 28. Thus, the oxygen in the atmosphere in the first chamber 24 can be pumped out to the external space, or the oxygen in the external space can be pumped into the first chamber 24.

A measuring electrode 36 having a substantially rectangular planar configuration and composed of a porous cermet electrode is formed in the close vicinity of the second diffusion rate-determining section 22 on an upper surface portion for forming the first chamber 24, of the upper surface of the first solid electrolyte layer 16d. A reference electrode 38 is formed on a lower surface portion exposed to the reference gas-introducing space 18, of the lower surface of the first solid electrolyte layer 16d. An electrochemical sensor cell, i.e., a controlling oxygen partial pressure-detecting cell 40 is constructed by the measuring electrode 36, the reference electrode 38, and the first solid electrolyte layer 16d.

The controlling oxygen partial pressure-detecting cell 40 is operated such that the partial pressure of oxygen in the atmosphere in the first chamber 24 can be detected by measuring the electromotive force V1 generated between the measuring electrode 36 and the reference electrode 38 by using a voltmeter 42, on the basis of the difference in oxygen concentration between the atmosphere in the first chamber 24 and the reference gas (atmospheric air) in the reference gas-introducing space 18.

The detected value of the partial pressure of oxygen is used to control the pumping voltage Vp0 of the variable power source 34 by the aid of a feedback control system 44. Specifically, the pumping operation effected by the main pumping cell 32 is controlled so that the partial pressure of oxygen in the atmosphere in the first chamber 24 has a predetermined value which is sufficiently low to make it possible to perform the control of the partial pressure of oxygen in the second chamber 26 in the next step. Each of the inner pumping electrode 28, the outer pumping electrode 30, and the measuring electrode 36 is composed of an inert material having a low catalytic activity on NOx, for example, NO contained in the measurement gas introduced into the first chamber 24.

Specifically, each of the inner pumping electrode 28 and the outer pumping electrode 30 may be composed of a porous cermet electrode. In this embodiment, each of the electrodes is composed of a metal such as Pt and a ceramic such as $ZrO_2$. Especially, it is necessary to use a material which has a weak reducing ability or no reducing ability with respect to the NO component in the measurement gas, for the inner pumping electrode 28 and the measuring electrode 36 disposed in the first chamber 24 to make contact with the measurement gas. It is preferable that each of the inner pumping electrode 28 and the measuring electrode 36 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

On the other hand, an auxiliary pumping electrode 50 having a substantially rectangular planar configuration and composed of a porous cermet electrode is formed on an entire lower surface portion for forming the second chamber 26, of the lower surface of the second solid electrolyte layer 16f. An auxiliary electrochemical pumping cell, i.e., an auxiliary pumping cell 52 is constructed by the auxiliary pumping electrode 50, the reference electrode 38, the second solid electrolyte layer 16f, the second spacer layer 16e, and the first solid electrolyte layer 16d.

A desired constant voltage Vp2 is applied between the auxiliary pumping electrode 50 and the reference electrode 38 of the auxiliary pumping cell 52 by the aid of an external power source 54. Thus, the oxygen in the atmosphere in the second chamber 26 can be pumped out to the reference gas-introducing space 18. Accordingly, the partial pressure of oxygen in the atmosphere in the second chamber 26 is controlled to have a low value of partial pressure of oxygen which does not substantially affects the measurement for the amount of the objective component under a condition in which the measurement gas component (NOx) is not substantially reduced or decomposed. In this arrangement, the change in amount of oxygen introduced into the second chamber 26 is greatly reduced as compared with the change in the measurement gas, owing to the operation of the main pumping cell 32 for the first chamber 24. Accordingly, the partial pressure of oxygen in the second chamber 26 is controlled accurately and constantly.

The gas sensor 10A according to the first embodiment further comprises a detecting electrode 60 having a substantially rectangular planar configuration and composed of a porous cermet electrode. The detecting electrode 60 is formed on an upper surface portion for forming the second chamber 26, separated from the second diffusion rate-determining section 22, of the upper surface of the first solid electrolyte layer 16d.

An electrochemical sensor cell, i.e., a measuring oxygen partial pressure-detecting cell 61 is constructed by the detecting electrode 60, the reference electrode 38, and the first solid electrolyte layer 16d. An electrochemical pumping cell, i.e., a measuring pumping cell 62 is constructed by the detecting electrode 60, the outer pumping electrode 30, the first solid electrolyte layer 16d interposed between the both electrodes 60, 30, the second spacer layers 16e, and the second solid electrolyte layer 16f.

The detecting electrode 60 is composed of, for example, a porous cermet comprising Rh as a metal capable of reducing NOx as the measurement gas component and zirconia as a ceramic. Accordingly, the detecting electrode 60 functions as a NOx-reducing catalyst for reducing NOx existing in the atmosphere in the second chamber 26.

In this embodiment, an electromotive force (electromotive force of the oxygen concentration cell) V2, which depends on the difference in oxygen concentration between the atmosphere around the detecting electrode 60 and the atmosphere around the reference electrode 38, is generated between the detecting electrode 60 and the reference electrode 38.

Therefore, in the gas sensor 10A according to the first embodiment, the electromotive force-measuring circuit 70 measures constantly the electromotive force V2 generated between the detecting electrode 60 and the reference electrode 38. The current supply circuit 14 controls the frequency of the pulse-shaped current signal Sif corresponding to a difference between an the electromotive force V2 measured by the electromotive force-measuring circuit 70 and the comparing voltage Vb. The pulse-shaped current signal Sif which is frequency-controlled on the basis of the electromotive force V2, is allowed to flow from the outer pumping electrode 30 to the detecting electrode 60. The measuring system 64 converts at least the frequency of the pulse-shaped current signal Sif into a concentration of NOx.

Accordingly, the partial pressure of oxygen in the atmosphere around the detecting electrode 60, in other words, the partial pressure of oxygen defined by the oxygen produced by the reduction or decomposition of the measurement gas component (NOx) is detected as an electric signal by measuring the electromotive force V2 generated between the detecting electrode 60 and the reference electrode 38 by using a measuring system 64 by the aid of the current supply circuit 14.

Figure 3:
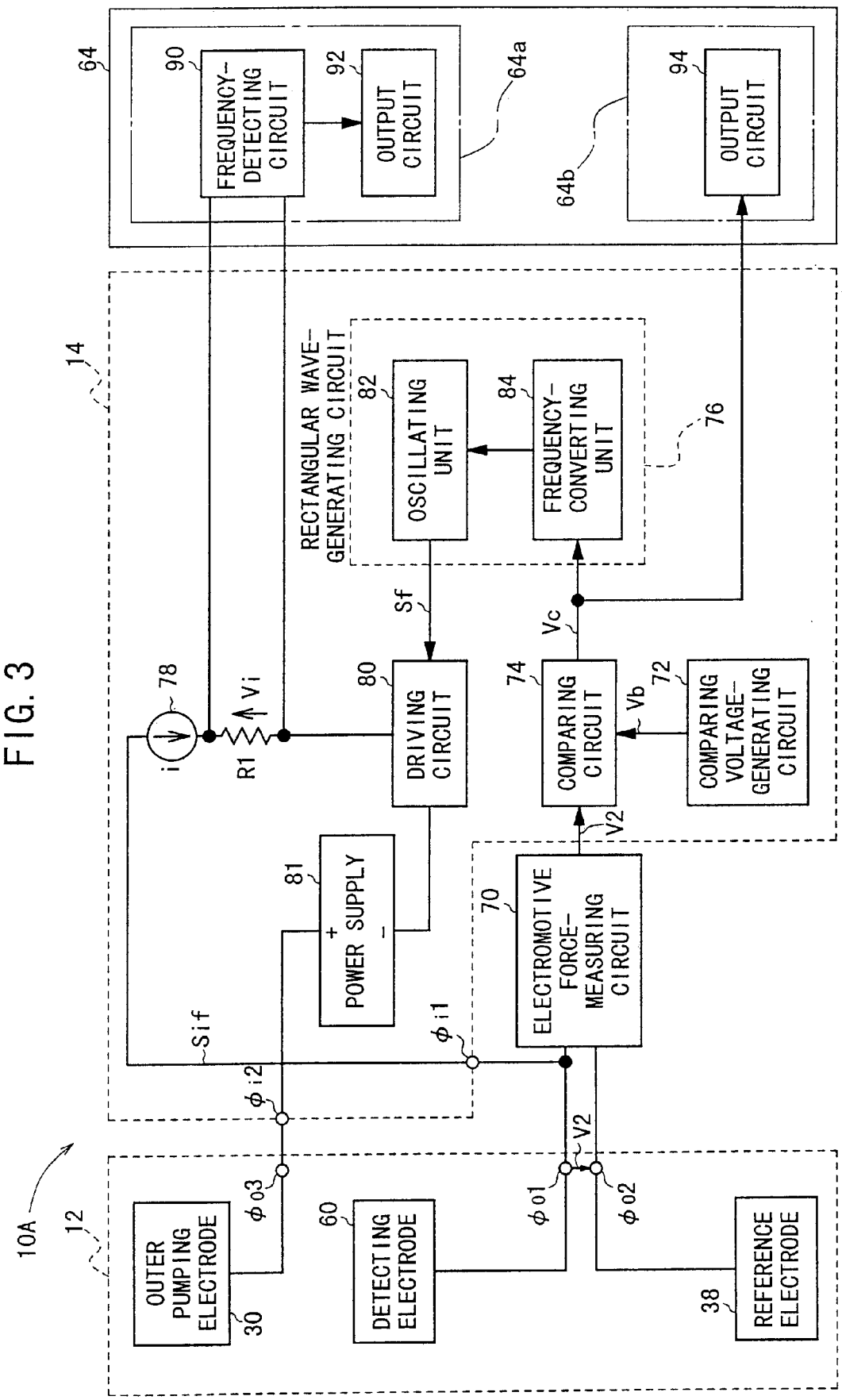
FIG. 3 shows a block diagram illustrating a circuit system of the gas sensor according to the first embodiment.

A first external output terminal φo1 electrically connected to the detecting electrode 60, a second external output terminal φo2 electrically connected to the reference electrode 38 and a third external output terminal φo3 electrically connected to the outer pumping electrode 30 are led to the outside of the main sensor device 12 respectively. As shown in FIG. 3, the first and second external output terminals φo1, φo2 are connected to input terminals of the electromotive force-measuring circuit 70 respectively. The first and third external output terminals φo1, φo3 are connected to first and second input terminal φi1, φi2 of the current supply circuit 14 respectively. Thus, the main sensor device 12, the electromotive force-measuring circuit 70 and the current supply circuit 14 are electrically connected to one another.

As shown in FIG. 2, the gas sensor 10A according to this embodiment further comprises a heater 66 for generating heat in accordance with electric power supply from the outside. The heater 66 is embedded in a form of being vertically interposed between the first and second substrate layers 16a, 16b. The heater 66 is provided in order to increase the conductivity of oxygen ion. An insulative layer 68 composed of alumina or the like is formed to cover upper and lower surfaces of the heater 66 so that the heater 66 is electrically insulated from the first and second substrate layers 16a, 16b.

The heater 66 is arranged over the entire portion ranging from the first chamber 24 to the second chamber 26. Accordingly, each of the first chamber 24 and the second chamber 26 is heated to a predetermined temperature. Simultaneously, each of the main pumping cell 32, the controlling oxygen partial pressure-detecting cell 40, and the measuring pumping cell 62 is also heated to a predetermined temperature and maintained at that temperature.

As shown in FIG. 3, the current supply circuit 14 of the gas sensor 10A according to the first embodiment comprises a comparing circuit 74 for determining a difference between the electromotive force V2 measured by the electromotive force-measuring circuit 70 and a comparing voltage Vb (for example, 450 mV) supplied from a comparing voltage-generating circuit 72 and amplifying the difference with a predetermined gain (for example, 100 times) to make an output as a measured voltage Vc, a rectangular wave-generating circuit 76 for outputting a rectangular wave signal Sf having a frequency corresponding to the level of the measured voltage Vc supplied from the comparing circuit 74, and a driving circuit 80 for performing ON-OFF control for a constant current i supplied from a constant current source 78, on the basis of the rectangular wave signal Sf supplied from the rectangular wave-generating circuit 76.

An output terminal of the driving circuit 80 is electrically connected to a negative terminal of the power supply 81. A positive terminal of the power supply 81 is electrically connected to the outer pumping electrode 30 via the second input terminal φi2 of the current supply circuit 14 and the third external output terminal ∠o3 of the main sensor device 12.

The rectangular wave-generating circuit 76 comprises an oscillating unit 82 for generating a rectangular wave having a predetermined crest value and having a predetermined pulse width, and a frequency-converting unit 84 for controlling an oscillation frequency of the oscillating unit 82 corresponding to the level of the measured voltage Vc supplied from the comparing circuit 74. The rectangular wave signal Sf, which has the frequency on the basis of the value of the electromotive force V2, is obtained from the rectangular wave-generating circuit 76.

In this embodiment, the pulse width of the rectangular wave is fixed to be, for example, 10 μsec. The crest value has a level necessary to perform ON-OFF control for the constant current i by the aid of the driving circuit 80. The circuit of the frequency-converting unit 84 is constructed such that the lower the value of the electromotive force V2 is, as with regard to the level of the comparing voltage Vb, the higher the frequency is.

The constant current source 78 and the driving circuit 80 are connected between the negative terminal of the power supply 81 and the first input terminal φi1 connected to the detecting electrode 60. In the first solid electrolyte layer 16d, the second spacer layer 16e and the second solid electrolyte layer 16f, the constant current i is allowed to flow from the outer pumping electrode 30 to the detecting electrode 60 only during a period of ON control effected by the driving circuit 80 (i.e., during a period corresponding to the pulse width of the rectangular wave signal Sf).

Figure 5:
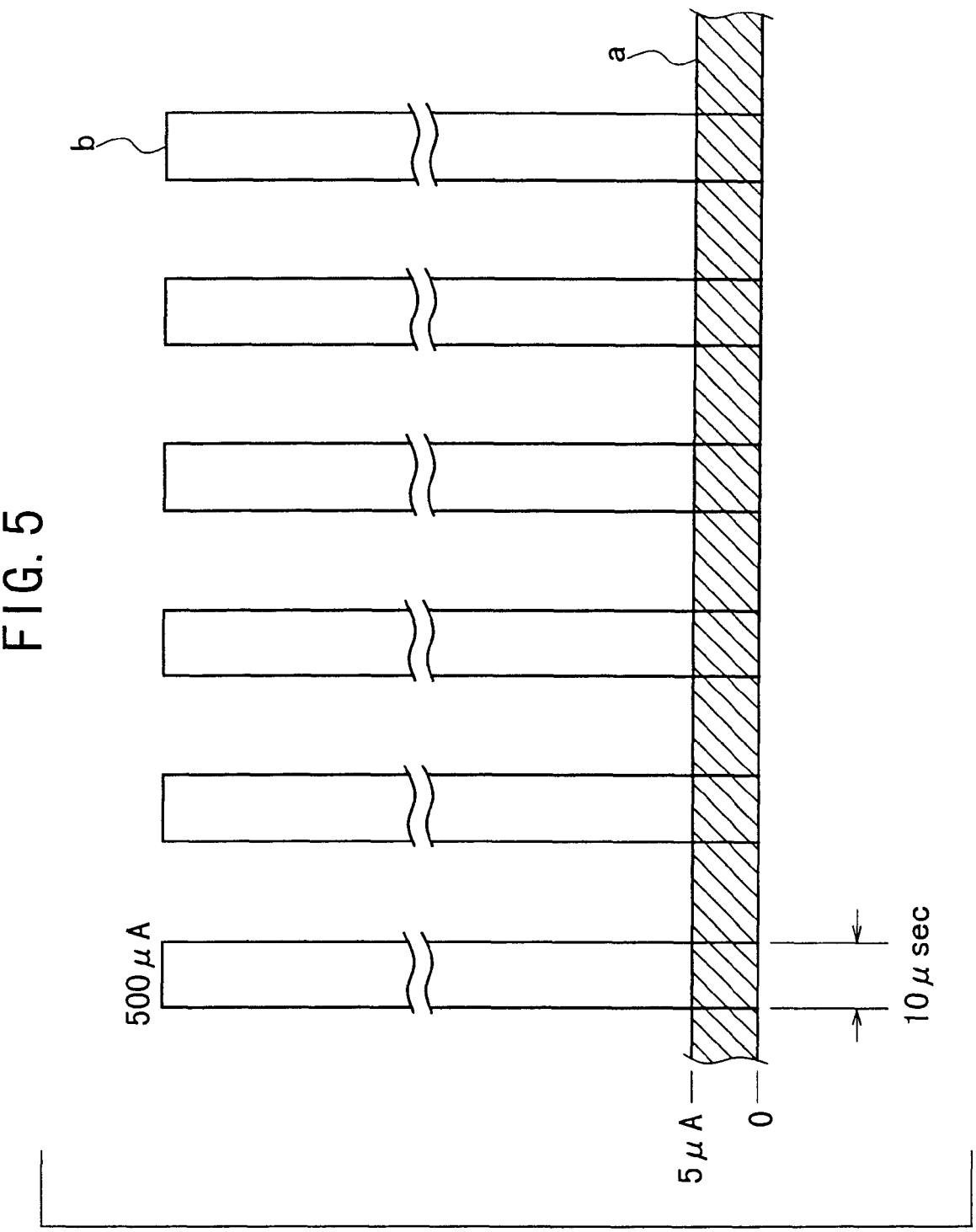
FIG. 5 shows waveforms illustrating a waveform of the pulse-shaped current signal used for the gas sensor according to the first embodiment, together with a direct current waveform.

In other words, the ON-OFF control for the constant current i effected by the driving circuit 80 provides a pulse-shaped current signal Sif in which the crest value is a predetermined value (for example, 500 μA) during the period corresponding to the pulse width of the rectangular wave signal Sf, and the crest value is, for example, 0 μA during the other periods (see a waveform "b" shown in FIG. 5).

Therefore, the constant current i flows from the reference electrode 38 to the detecting electrode 60 during the period corresponding to the pulse width of the rectangular wave signal Sf outputted from the rectangular wave-generating circuit 76. The oxygen, which is in an amount corresponding to a quantity of electricity represented by the crest value (for example, 500 μA) of the constant current i×the pulse width of the rectangular wave signal Sf, is pumped from the second chamber 26 to the external space.

The pumping operation causes a change in partial pressure of oxygen in the second chamber 26. The change is measured as the electromotive force V2 between the detecting electrode 60 and the reference electrode 38 by the aid of the electromotive force-measuring circuit 70. The rectangular wave signal Sf, which has a frequency corresponding to the electromotive force V2, is supplied to the driving circuit 80. Thus, the constant current i flows from the outer pumping electrode 30 to the detecting electrode 60 during the period corresponding to the pulse width of the rectangular wave signal Sf.

Figure 4:
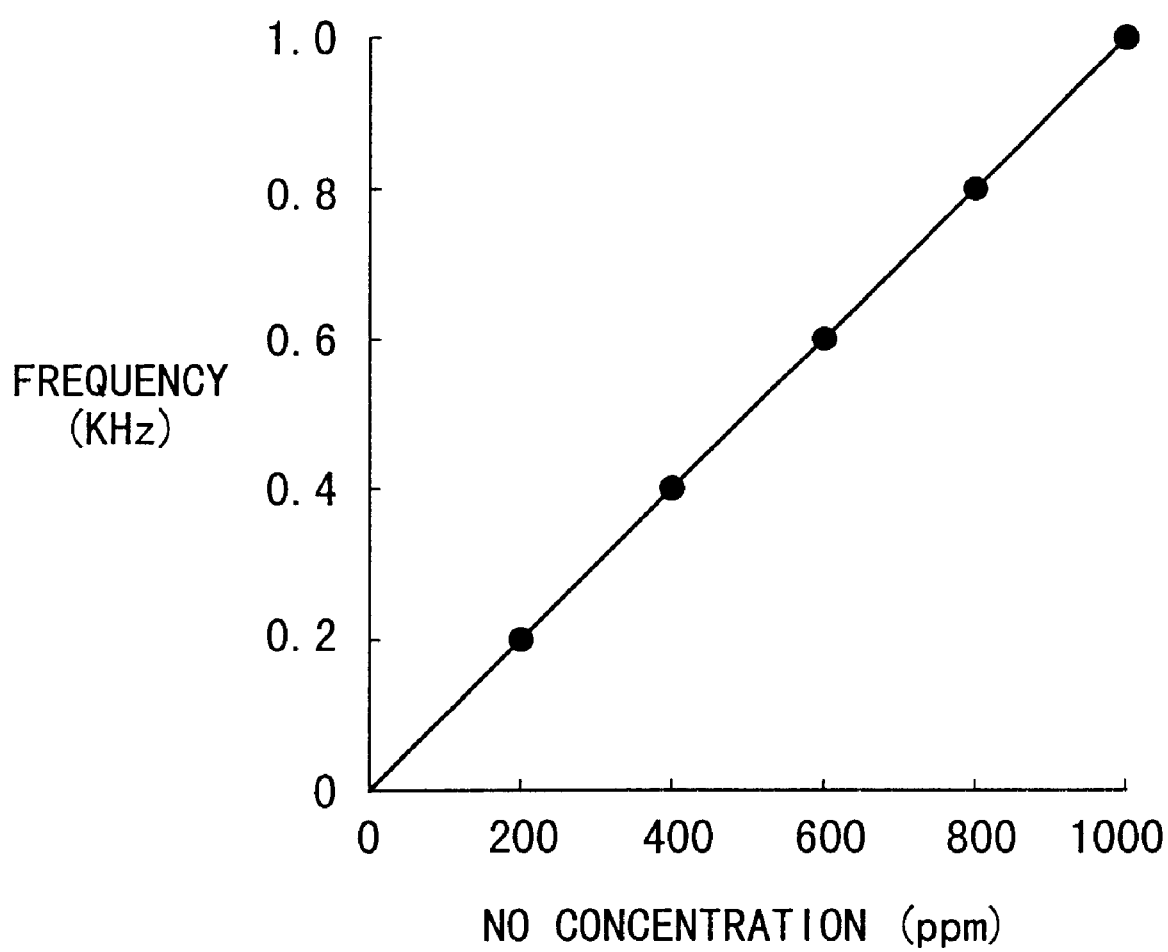
FIG. 4 shows a characteristic curve illustrating the change in frequency of a pulse-shaped current signal with respect to the change in NO concentration concerning the gas sensor according to the first embodiment.

A characteristic shown in FIG. 4 represents a relationship between the NO concentration and the frequency of the rectangular wave signal Sf concerning the gas sensor 10A according to the first embodiment. According to the characteristic, it is understood that the frequency is linearly increased in response to the NO concentration, making it possible to measure the NO concentration.

On the other hand, as shown in FIG. 3, for example, two types of circuits are conceived for the measuring system 64. The first measuring system 64a comprises a resistor R1 for extracting, as a voltage signal Vi, the constant current i subjected to the ON-OFF control effected by the driving circuit 80, a frequency-detecting circuit 90 for detecting the frequency of the voltage signal Vi extracted by the aid of the resistor R1, and an output circuit 92 for converting the frequency value detected by the frequency-detecting circuit 90 on the basis of, for example, the characteristic shown in FIG. 4 into the NO concentration so that the concentration value is displayed, for example, by digital expression. The second measuring system 64b comprises an output circuit 94 for converting the measured voltage Vc supplied from the comparing circuit 74 into the NO concentration so that the concentration value is displayed, for example, by digital expression.

The second measuring system 64b is available because of the following reason. That is, the frequency may be measured by detecting the timing of the flow of the constant current i to measure the frequency thereof, as performed in the first measuring system 64a. However, the voltage which enters the frequency-converting unit of the rectangular wave-generating circuit 76, i.e., the measured voltage Vc based on the difference between the comparing voltage Vb supplied from the comparing voltage-generating circuit 72 and the electromotive force V2 between the detecting electrode 60 and the reference electrode 38 directly represents the frequency to be used for the control. The detection of the measured voltage Vc is equivalent to the measurement of the frequency of the pulse-shaped current signal Sif. Especially, in the second measuring system 64b, it is unnecessary to provide any circuit which is exclusively used to measure the frequency of the pulse-shaped current signal Sif, making it possible to effectively simplify the circuit arrangement.

The gas sensor 10A according to the first embodiment is basically constructed as described above. Next, its operation and effect will be explained.

At first, the electromotive force V2 between the reference electrode 38 and the detecting electrode 60 of the gas sensor 10A is measured by the electromotive force-measuring circuit 70. The electromotive force V2 is compared with the comparing voltage Vb in the comparing circuit 74. The comparing circuit 74 determines the difference between the electromotive force V2 and the comparing voltage Vb. The difference is amplified with the predetermined gain to be outputted as the measured voltage Vc.

The measured voltage Vc is introduced into the frequency-converting unit 84 for adjusting the frequency of the rectangular wave signal Sf outputted from the rectangular wave-generating circuit 76. The frequency-converting unit 84 controls the oscillation frequency of the oscillating unit 82 on the basis of the measured voltage Vc. Accordingly, the rectangular wave signal Sf is obtained, which has the frequency based on the value of the electromotive force V2.

The rectangular wave signal Sf, which is outputted from the rectangular wave-generating circuit 76, is introduced into the driving circuit 80. The driving circuit 80 performs the ON-OFF control for the constant current i supplied from the constant current source 78, on the basis of the rectangular wave signal Sf. The process is performed such that the constant current i is allowed to flow during only the period corresponding to the pulse width of the rectangular wave signal Sf, and the flow of the constant current i is stopped during the other periods. Accordingly, the pulse-shaped signal Sif flows from the reference electrode 38 to the detecting electrode 60.

In the case of the first measuring system 64a, the frequency of the voltage signal Vi detected by the resistor R1 is detected by the frequency-detecting circuit 90. The frequency value detected by the frequency-detecting circuit 90 is converted into the NOx concentration by the output circuit 92, and it is displayed, for example, by digital expression. In the case of the second measuring system 64b, the measured voltage Vc supplied from the comparing circuit 74 is converted into the NOx concentration by the output circuit 94, and it is displayed, for example, by digital expression.

As described above, in the gas sensor 10A according to the first embodiment, the pulse-shaped current signal Sif, which is frequency-controlled on the basis of the electromotive force V2 generated between the detecting electrode 60 and the reference electrode 38, is allowed to flow from the outer pumping electrode 30 to the detecting electrode 60. Therefore, the following effect can be obtained.

In the case of the conventional measuring method, for example, a concentration of 1000 ppm can be merely detected with a low current value in which the pumping current of the gas sensor is 5 $\mu$A. The system tends to be affected by the external electric noise because the current is small. However, in the case of the gas sensor 10A according to the first embodiment, the measuring system 64 (for example, the first measuring system 64a) is used to measure the frequency of the pulse-shaped current signal Sif having the crest value of 500 $\mu$A. Therefore, for example, when the critical value is set to be 250 $\mu$A to measure the frequency of the current signal Sif, it is possible to accurately measure the NOx concentration, for example, even if the noise component exists in an amount corresponding to 100 $\mu$A.

Next, a specified example of the gas sensor 10A according to the first embodiment described above will be explained while making comparison with a case in which a direct current is allowed to flow from the reference electrode 38 to the detecting electrode 60.

At first, when the direct current is allowed to flow, for example, the direct current is 5 $\mu$A for a concentration of NO of 1000 ppm as shown in a waveform "a" in FIG. 5.

Assuming that the period of time is 1 sec, the quantity of electricity is 5 $\mu$A·sec=5$\mu$ coulombs when the direct current flows. On the other hand, in the gas sensor 10A according to the first embodiment, the pulse-shaped current signal Sif (see a waveform "b"), which has a quantity of electricity equivalent to the quantity of electricity (5$\mu$coulombs), is allowed to flow from the outer pumping electrode 30 to the detecting electrode 60. Simultaneously, for example, the frequency-detecting circuit 90 is used to count the number of pulses of the voltage signal Vi per unit time. In other words, the frequency of the pulse of the current signal Sif (exactly, the rectangular wave signal Sf) is controlled so as to provide the same value as the direct current value of the direct current (5 $\mu$A)×unit time (1 sec).

In the case of the specified example described above, the quantity of electricity possessed by one pulse is 10 $\mu$sec×500 $\mu$A=5000×10$^{-6}$$\mu$ coulombs=5×10$^{-3}$$\mu$ coulombs which is 1/1000 of that used for the direct current. Therefore, when 1000 individuals of pulses are allowed to flow for 1 sec, i.e., when the pulse-shaped current signal Sif having a frequency of 1 kHz is allowed to flow, then it is possible to perform the aimed pumping operation (the pumping operation for making the partial pressure of oxygen in the second chamber 26 to be the partial pressure of oxygen corresponding to the comparing voltage Vb). Simultaneously, it is possible to measure the NO concentration highly accurately without being affected by the electric noise.

Generally, some main sensor devices 12 have large limiting currents, and other main sensor devices 12 have small limiting currents, because of, for example, dispersion in production. When the same NOx concentration is measured, the main sensor device 12 having a large limiting current provides the current signal Sif having a high frequency as compared with the main sensor device 12 having a small limiting current. There is a possibility of occurrence of any measurement error.

In order to solve the foregoing problem, the conventional method has relied on, for example, the shunt resistor system or the voltage divider resistor system. However, any of them has such an inconvenience that it is necessary to increase the number of lead wires, which is disadvantageous in view of the cost.

A modified embodiment (10A$a$) of the gas sensor 10A according to the first embodiment described below provides a gas sensor which makes it possible to solve the problem as described above. The gas sensor 10A$a$ will be explained with reference to FIG. 6. Components or parts corresponding to those shown in FIG. 3 are designated by the same reference numerals.

Figure 6:
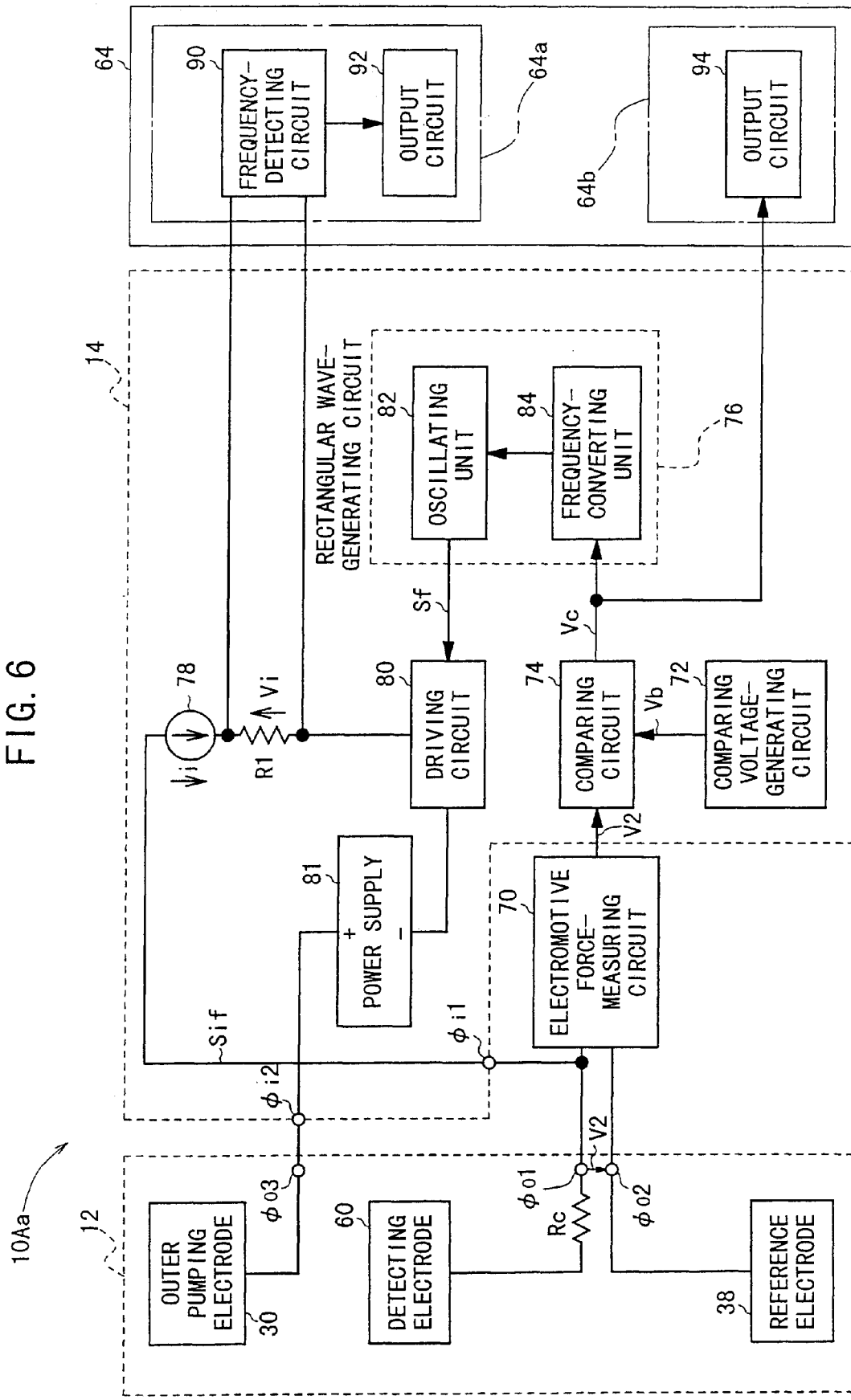
FIG. 6 shows a block diagram illustrating a circuit system of a gas sensor according to a modified embodiment of the first embodiment.

As shown in FIG. 6, the gas sensor 10A$a$ according to the modified embodiment is constructed in approximately the same manner as in the gas sensor 10A according to the first embodiment described above (see FIG. 3). However, the former is different from the latter in that an adjusting resistor Rc is connected in series to the supply line for the current signal Sif from the current supply circuit 14. In the illustrated embodiment, the adjusting resistor Rc is connected in series between the detecting electrode 60 and the first external output terminal $\phi$o1 of the main sensor device 12.

It is now assumed a case in which the electric potential of the negative terminal of the power supply 81 is set to be, for example, −5 V, the voltage between the reference electrode 38 and the detecting electrode 60 is, for example, 5 V, the value of the adjusting resistor Rc is set to be, for example, 10 kΩ, and the alternating current impedance between the detecting electrode 60 and the outer pumping electrode 30 of the main sensor device 12 is set to be about 300 Ω.

The direct current impedance between the detecting electrode 60 and the outer pumping electrode 30 is about 2 kΩ. However, in the case of the alternating current having a high frequency, for example, a frequency of not less than 10 kHz, the impedance is about 1/5 to 1/10 thereof. The impedance is also sufficiently small for the rectangular wave signal containing a lot of high frequency components, as compared with those for the direct current. That is, the impedance has a value in such a degree that it can be sufficiently neglected with respect to the adjusting resistor Rc.

Accordingly, the current signal Sif, which flows from the outer pumping electrode 30 to the detecting electrode 60 in accordance with the driving operation of the current supply circuit 14, is a current signal Sif with pulses having a crest value of 500 $\mu$A. The crest value is determined by the size of the adjusting resistor Rc.

Therefore, the following operation is available for a gas sensor in which the main sensor device 12 has a large limiting current, for example, for a gas sensor in which, for example, a direct current of 7 $\mu$A is allowed to flow, for example, for a NOx concentration of 1000 ppm, when the measurement is performed by supplying the direct current. That is, when the resistance value of the adjusting resistor Rc is lowered, and the value of the constant current i flowing between the outer pumping electrode 30 and the detecting electrode 60 is set to be, for example, 700 $\mu$A, then such a sensor behaves equivalently to a gas sensor in which a current of 5 $\mu$A is allowed to flow for the NOx concentration of 1000 ppm.

As described above, in the gas sensor 10A$a$ according to the modified embodiment, the relationship between the NOx concentration and the pulse frequency can be consequently maintained to be constant only by changing the value of the adjusting resistor Rc, irrelevant to the dispersion (for example, any dispersion in sensitivity) among individual main sensor devices 12. Thus, it is unnecessary to adopt the conventional shunt resistor system and the conventional voltage divider resistor system.

In other words, the gas sensor 10A$a$ according to the modified embodiment makes it possible to compensate the dispersion (dispersion in crest value or output) among individual sensors without increasing the number of lead wires and terminals, which is advantageous in view of the production cost.

Next, a gas sensor 10B according to a second embodiment will be explained with reference to FIG. 7. Components or parts corresponding to those shown in FIG. 3 are designated by the same reference numerals.

Figure 7:
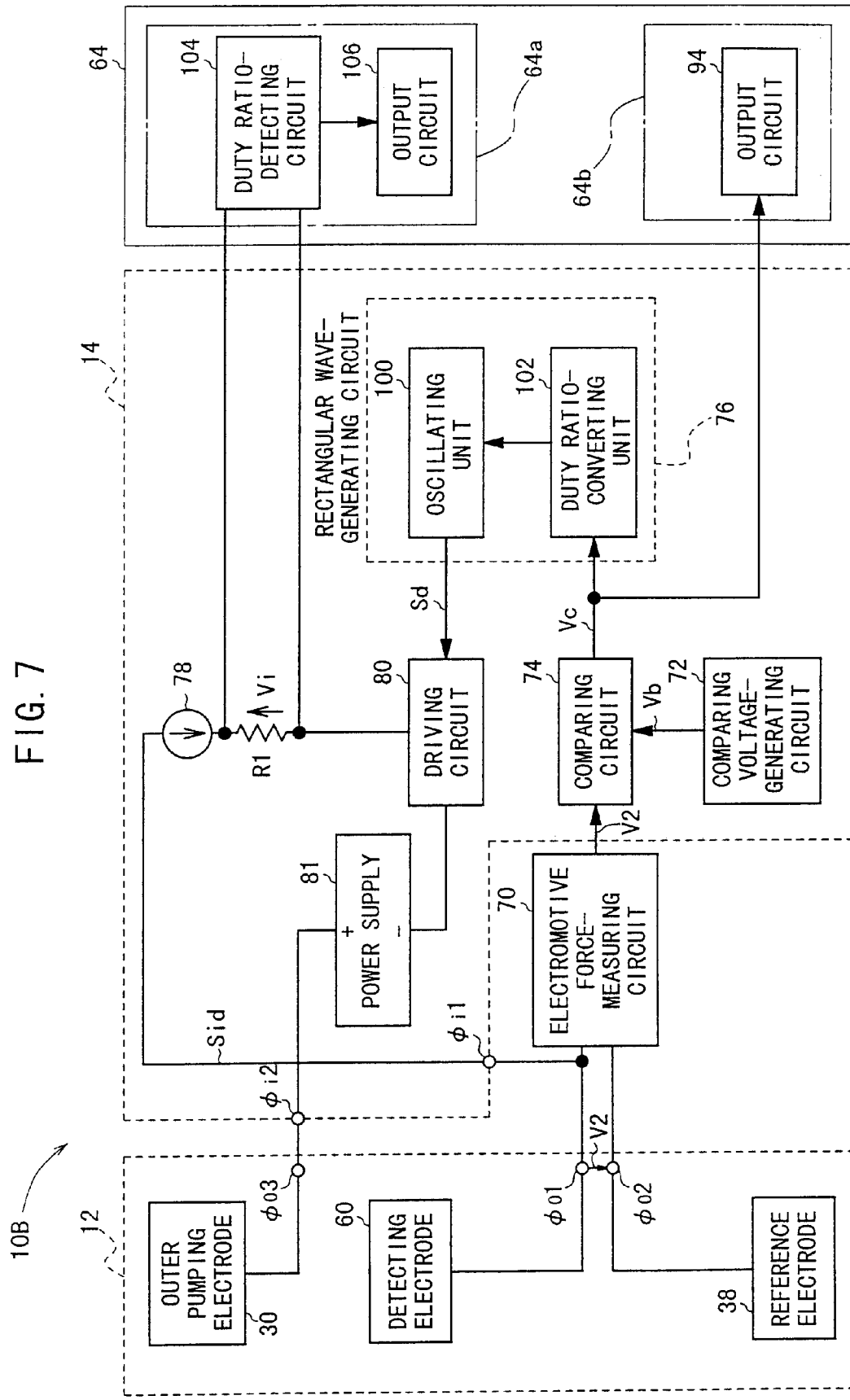
FIG. 7 shows a block diagram illustrating a circuit system of a gas sensor according to a second embodiment.

As shown in FIG. 7, the gas sensor 10B according to the second embodiment is constructed in approximately the same manner as in the gas sensor 10A according to the first embodiment described above (see FIG. 3). However, the former is different from the latter in that the rectangular wave-generating circuit 76 of the current supply circuit 14 comprises an oscillating unit 100 for generating a rectangular wave having a predetermined crest value and having a predetermined pulse width, and a duty ratio-converting unit 102 for controlling the duty ratio (the ratio of ON/OFF time) of the pulse signal outputted from the oscillating unit 100, depending on the level of the measured voltage Vc supplied from the comparing circuit 74. A rectangular wave signal Sd, which has the duty ratio based on the value of the electromotive force V2, is obtained from the rectangular wave-generating circuit 76.

The frequency of the pulse signal outputted from the oscillating unit 100 is fixed to be, for example, 100 Hz. The crest value has a level necessary to perform ON-OFF control for the constant current i by the aid of the driving circuit 80 disposed at the downstream stage. The circuit of the duty ratio-converting unit 102 is constructed such that the lower the value of the electromotive force V2 is, as with regard to the level of the comparing voltage Vb, the higher the duty ratio is (the longer the period of the pulse width Pw is (see FIG. 9)).

Figure 9:
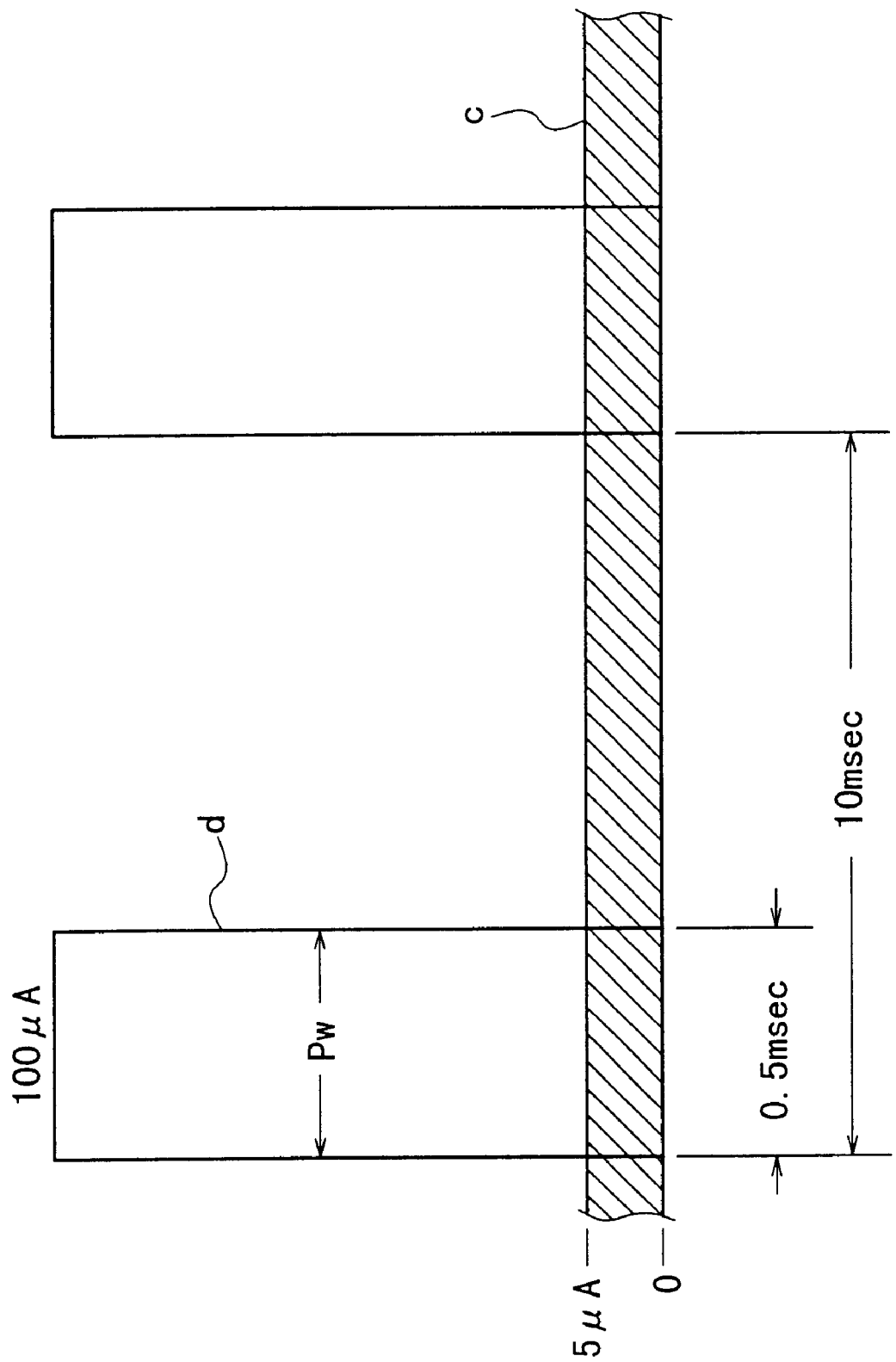
FIG. 9 shows waveforms illustrating a waveform of the pulse-shaped current signal used for the gas sensor according to the second embodiment, together with a direct current waveform.

In other words, the ON-OFF control for the constant current i effected by the driving circuit 80 provides a pulse-shaped current signal Sid in which the crest value is a predetermined value (for example, 100 $\mu$A) during the period corresponding to the pulse width Pw of the rectangular wave signal Sd, and the crest value is, for example, 0 $\mu$A during the other periods (see a waveform "d" shown in FIG. 9). Since the frequency of the pulse signal outputted from the oscillating unit 100 is 100 Hz, the frequency of the current signal Sid is fixed to the same frequency of 100 Hz.

Figure 8:
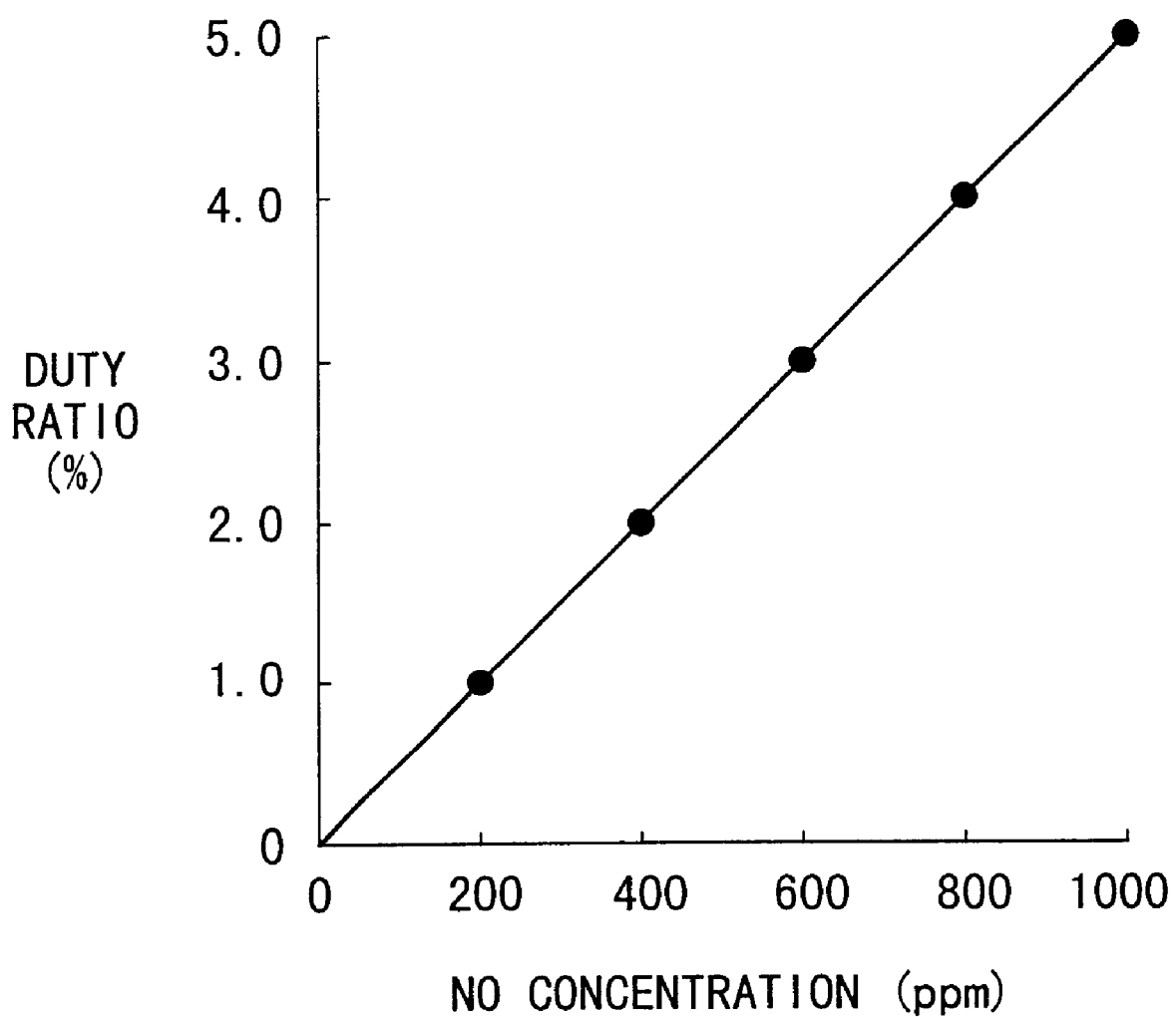
FIG. 8 shows a characteristic curve illustrating the change in duty ratio of a pulse-shaped current signal with respect to the change in NO concentration concerning the gas sensor according to the second embodiment.

A characteristic shown in FIG. 8 represents a relationship between the NO concentration and the duty ratio of the current signal Sid concerning the gas sensor 10B according to the second embodiment. According to the characteristic, it is understood that the duty ratio (ON time) is linearly increased in response to the NO concentration, making it possible to measure the NO concentration.

As for the measuring system 64, for example, two types of circuits are conceived in the second embodiment as well. As shown in FIG. 7, the first measuring system 64$a$ comprises a duty ratio-detecting circuit 104 for detecting the duty ratio (for example, the pulse width Pw) of the voltage signal Vi extracted by the aid of the resistor R1, and an output circuit 106 for converting the duty ratio detected by the duty ratio-detecting circuit 104 on the basis of, for example, the characteristic shown in FIG. 8 into the NO concentration so that the concentration value is displayed, for example, by digital expression.

On the other hand, the second measuring system 64b comprises an output circuit 94 for converting the measured voltage Vc supplied from the comparing circuit 74 into the NO concentration so that the concentration value is displayed, for example, by digital expression. The duty ratio may be measured by detecting the voltage signal Vi to measure the duty ratio thereof, as performed in the first measuring system 64a. However, the voltage which enters the duty ratio-converting unit 102 of the rectangular wave-generating circuit 76, i.e., the measured voltage Vc based on the difference between the comparing voltage Vb supplied from the comparing voltage-generating circuit 72 and the electromotive force V2 between the detecting electrode 60 and the reference electrode 38 directly represents the duty ratio. The detection of the measured voltage Vc is equivalent to the measurement of the duty ratio of the pulse-shaped current signal Sid. Therefore, in the second measuring system 64b, it is unnecessary to provide any circuit which is exclusively used to measure the duty ratio of the voltage signal Vi, making it possible to effectively simplify the circuit arrangement.

The gas sensor 10B according to the second embodiment is basically constructed as described above. Next, its operation and effect will be explained.

At first, the electromotive force V2 between the reference electrode 38 and the detecting electrode 60 of the gas sensor 10B is measured by the electromotive force-measuring circuit 70. The electromotive force V2 is compared with the comparing voltage Vb in the comparing circuit 74. The comparing circuit 74 determines the difference between the electromotive force V2 and the comparing voltage Vb. The difference is amplified with the predetermined gain to be outputted as the measured voltage Vc.

The measured voltage Vc is introduced into the duty ratio-converting unit 102 for adjusting the duty ratio of the rectangular wave signal Sd outputted from the rectangular wave-generating circuit 76. The duty ratio-converting unit 102 controls the duty ratio (the pulse width Pw) of the pulse signal outputted from the oscillating unit 100, on the basis of the measured voltage Vc. Accordingly, the rectangular wave signal Sd is obtained, which has the duty ratio based on the value of the electromotive force V2.

The rectangular wave signal Sd, which is outputted from the rectangular wave-generating circuit 76, is introduced into the driving circuit 80. The driving circuit 80 performs the ON-OFF control for the constant current i on the basis of the rectangular wave signal Sd. The process is performed such that the constant current i is allowed to flow during only the period corresponding to the pulse width Pw of the rectangular wave signal Sd, and the flow of the constant current i is stopped during the other periods. Accordingly, the pulse-shaped signal Sid flows from the outer pumping electrode 30 to the detecting electrode 60.

In the case of the first measuring system 64a, the duty ratio of the voltage signal Vi detected by the resistor R1 is detected by the duty ratio-detecting circuit 104. The duty ratio detected by the duty ratio-detecting circuit 104 is converted into the NOx concentration by the output circuit 106, and it is displayed, for example, by digital expression.

In the case of the second measuring system 64b, the measured voltage Vc supplied from the comparing circuit 74 is converted into the NOx concentration by the output circuit 94, and it is displayed, for example, by digital expression.

As described above, in the gas sensor 10B according to the second embodiment, the pulse-shaped current signal Sid, which is controlled for the duty ratio on the basis of the electromotive force V2 generated between the detecting electrode 60 and the reference electrode 38, is allowed to flow from the outer pumping electrode 30 to the detecting electrode 60. Therefore, the following effect can be obtained.

In the case of the conventional measuring method, for example, a concentration of 1000 ppm can be merely detected with a low current value in which the pumping current of the gas sensor is 5 $\mu$A. The system tends to be affected by the external electric noise because the current is small. However, in the case of the gas sensor 10B according to the second embodiment, the measuring system 64 is used to measure the duty ratio of the pulse-shaped current signal Sid, i.e., the pulse width Pw which is the time, having the crest value of 100 $\mu$A at a frequency of, for example, 100 Hz. Therefore, the system is scarcely affected by the noise, and it is possible to accurately measure the NOx concentration.

Next, a specified example of the gas sensor 10B according to the second embodiment described above will be explained while making comparison with a case in which a direct current is allowed to flow from the reference electrode 38 to the detecting electrode 60.

At first, when the direct current is allowed to flow, for example, the direct current is 5 $\mu$A for a concentration of NO of 1000 ppm as shown in a waveform "c" in FIG. 9.

Assuming that there is given one cycle=10 msec for the pulse signal outputted from the oscillating unit 100, the quantity of electricity is 5 $\mu$A·10 msec=50×10$^{-3}$ $\mu$A·sec= 50×10$^{-3}$$\mu$ coulombs when the direct current flows.

On the other hand, in the gas sensor 10B according to the second embodiment, the pulse-shaped electric signal Sid, which has a quantity of electricity equivalent to the quantity of electricity (50×10$^{-3}$$\mu$ coulombs), is allowed to flow from the reference electrode 38 to the detecting electrode 60. Simultaneously, for example, the duty ratio-detecting circuit 104 is used to measure the pulse width Pw of the voltage signal Vi. That is, the duty ratio of the pulse of the current signal Sid (exactly, the rectangular wave signal Sd), in other words, the pulse width Pw is controlled so as to provide the same value as the direct current value of the direct current (5 $\mu$A)×unit time (10 msec).

In the case of the specified example described above, the pulse width Pw, which is equivalent to the quantity of electricity of 50×10$^{-3}$$\mu$ coulombs is (50×10$^{-3}$ $\mu$A·sec)/100 $\mu$A=0.5 msec. The duty ratio is 0.5 msec/10 msec which is 1/20. Therefore, when the pulse signal having the duty ratio of 1/20, i.e., the pulse-shaped current signal Sid having the pulse width Pw of 0.5 msec is allowed to flow, then it is possible to perform the aimed pumping operation (the pumping operation for making the partial pressure of oxygen in the second chamber 26 to be the partial pressure of oxygen corresponding to the comparing voltage Vb). Simultaneously, it is possible to measure the NO concentration highly accurately without being affected by the electric noise.

Figure 10:
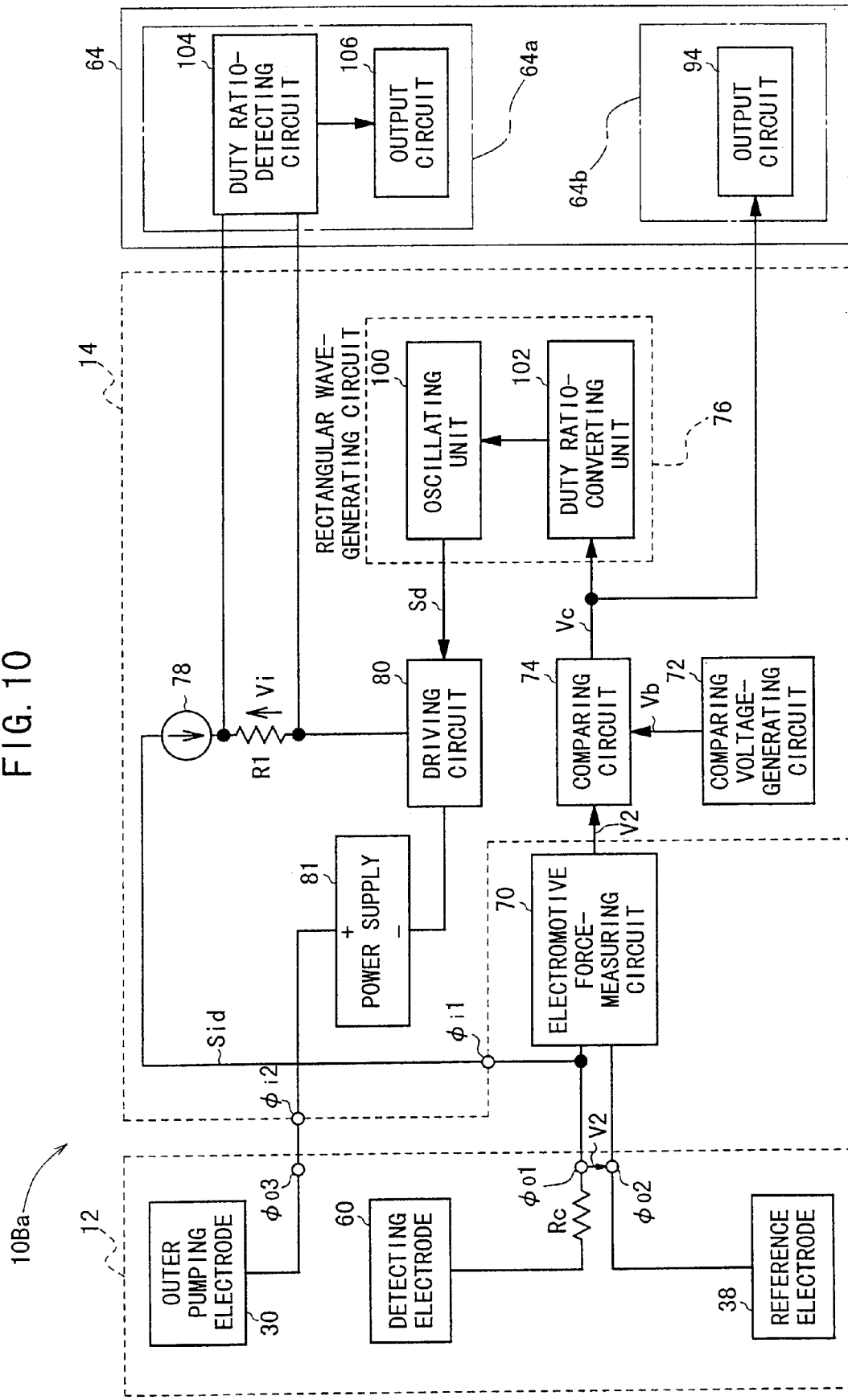
FIG. 10 shows a block diagram illustrating a circuit system of a gas sensor according to a modified embodiment of the second embodiment.

Next, a modified embodiment (10Ba) of the gas sensor 10B according to the second embodiment will be explained with reference to FIG. 10. Components or parts corresponding to those shown in FIG. 7 are designated by the same reference numerals.

Some main sensor devices 12 have large limiting currents, and other main sensor devices 12 have small limiting currents, because of, for example, dispersion in production. When the same NOx concentration is measured, the main sensor device 12 having a large limiting current provides a high duty ratio (a long pulse width Pw) as compared with the main sensor device 12 having a small limiting current. There is a possibility of occurrence of any measurement error.

The gas sensor 10Ba according to the modified embodiment eliminates any measuring error which would be otherwise caused by the dispersion among individual main sensor devices 12. As shown in FIG. 10, the gas sensor 10Ba according to the modified embodiment is constructed in approximately the same manner as in the gas sensor 10B according to the second embodiment described above (see FIG. 7). However, the former is different from the latter in that an adjusting resistor Rc is connected in series to the supply line for the current signal Sid from the current supply circuit 14. In the illustrated embodiment, the adjusting resistor Rc is connected between the detecting electrode 60 and the first external output terminal φo1 of the main sensor device 12.

It is now assumed a case in which the electric potential of the negative terminal of the power supply 81 is set to be, for example, −5 V, the voltage between the reference electrode 38 and the detecting electrode 60 is, for example, 5 V, the value of the adjusting resistor Rc is set to be, for example, 50 kΩ, and the alternating current impedance between the detecting electrode 60 and the outer pumping electrode 30 of the main sensor device 12 is set to be about 300 Ω. The current, which flows from the outer pumping electrode 30 to the detecting electrode 60 in accordance with the driving operation of the current supply circuit 14, is a current signal Sid with pulses having a frequency of 100 Hz and having a crest value of 100 μA. The crest value is determined by the size of the adjusting resistor Rc.

Therefore, the following operation is available for a gas sensor in which the main sensor device 12 has a large limiting current, for example, for a gas sensor in which, for example, a direct current of 7 μA is allowed to flow, for example, for a NOx concentration of 1000 ppm. That is, when the resistance value of the adjusting resistor Rc is lowered, and the value of the constant current i flowing between the outer pumping electrode 30 and the detecting electrode 60 is set to be, for example, 140 μA, then such a sensor behaves equivalently to a gas sensor in which a current of 5 μA is allowed to flow for the NOx concentration of 1000 ppm.

As described above, in the gas sensor 10Ba according to the modified embodiment, the relationship between the NOx concentration and the pulse frequency can be consequently maintained to be constant only by changing the value of the adjusting resistor Rc, irrelevant to the dispersion (for example, any dispersion in sensitivity) among individual main sensor devices 12. Thus, it is unnecessary to adopt the conventional shunt resistor system and the conventional voltage divider resistor system.

In other words, the gas sensor 10Ba according to the modified embodiment makes it possible to compensate the dispersion (dispersion in crest value or output) among individual sensors without increasing the number of lead wires and terminals, which is advantageous in view of the production cost.

Next, a gas sensor 10C according to a third embodiment will be explained with reference to FIGS. 11 to 14. Components or parts corresponding to those shown in FIG. 3 are designated by the same reference numerals.

Figure 11:
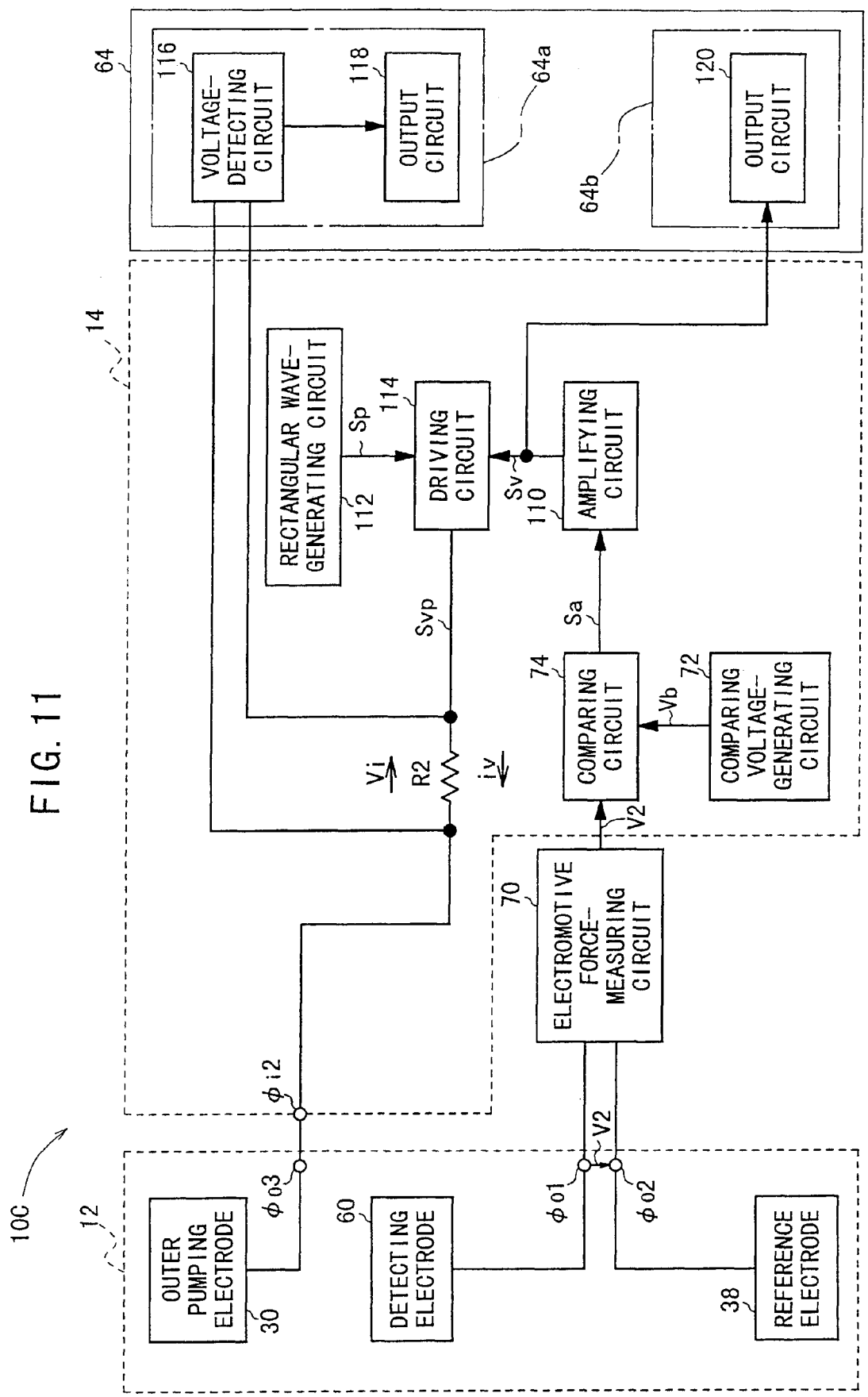
FIG. 11 shows a block diagram illustrating a circuit system of a gas sensor according to a third embodiment.

As shown in FIG. 11, the gas sensor 10C according to the third embodiment is constructed in approximately the same manner as in the gas sensor 10A according to the first embodiment described above (see FIG. 3). However, the former is different from the latter in the arrangement of the current supply circuit 14 as follows.

That is, as shown in FIG. 11, the current supply circuit 14 comprises a comparing circuit 74 for determining a difference between the electromotive force V2 measured by the electromotive force-measuring circuit 70 and a comparing voltage Vb (for example, 450 mV) supplied from a comparing voltage-generating circuit 72 and outputting it as a voltage signal Sa, an amplifying circuit 110 for amplifying the voltage signal Sa supplied from the comparing circuit 74, for example, 500 times to give a measured voltage signal Sv, a rectangular wave-generating circuit 112 for generating a pulse signal Sp having a frequency of 1 kHz and having a duty ratio of, for example, 1/1000 (ON period: 1 μsec, OFF period: 999 μsec), and a driving circuit 114 for performing ON-OFF control for the measured voltage signal Sv supplied from the amplifying circuit 110, on the basis of the pulse signal Sp (rectangular wave) supplied from the rectangular wave-generating circuit 112.

An output line of the driving circuit 114 is electrically connected to the second input terminal φi2 so that a current iv, which corresponds to the voltage outputted from the driving circuit 114, is supplied to the outer pumping electrode 30. The current iv is detected as a voltage Vi by the aid of a current-detecting resistor R2 (for example 10 kΩ) connected and inserted between the driving circuit 114 and the second input terminal φi2.

A pulse-shaped driving signal Svp (voltage signal), which has a constant frequency and a constant duty ratio and which has a voltage level based on the value of the electromotive force V2, is obtained from the driving circuit 114.

Figure 13:
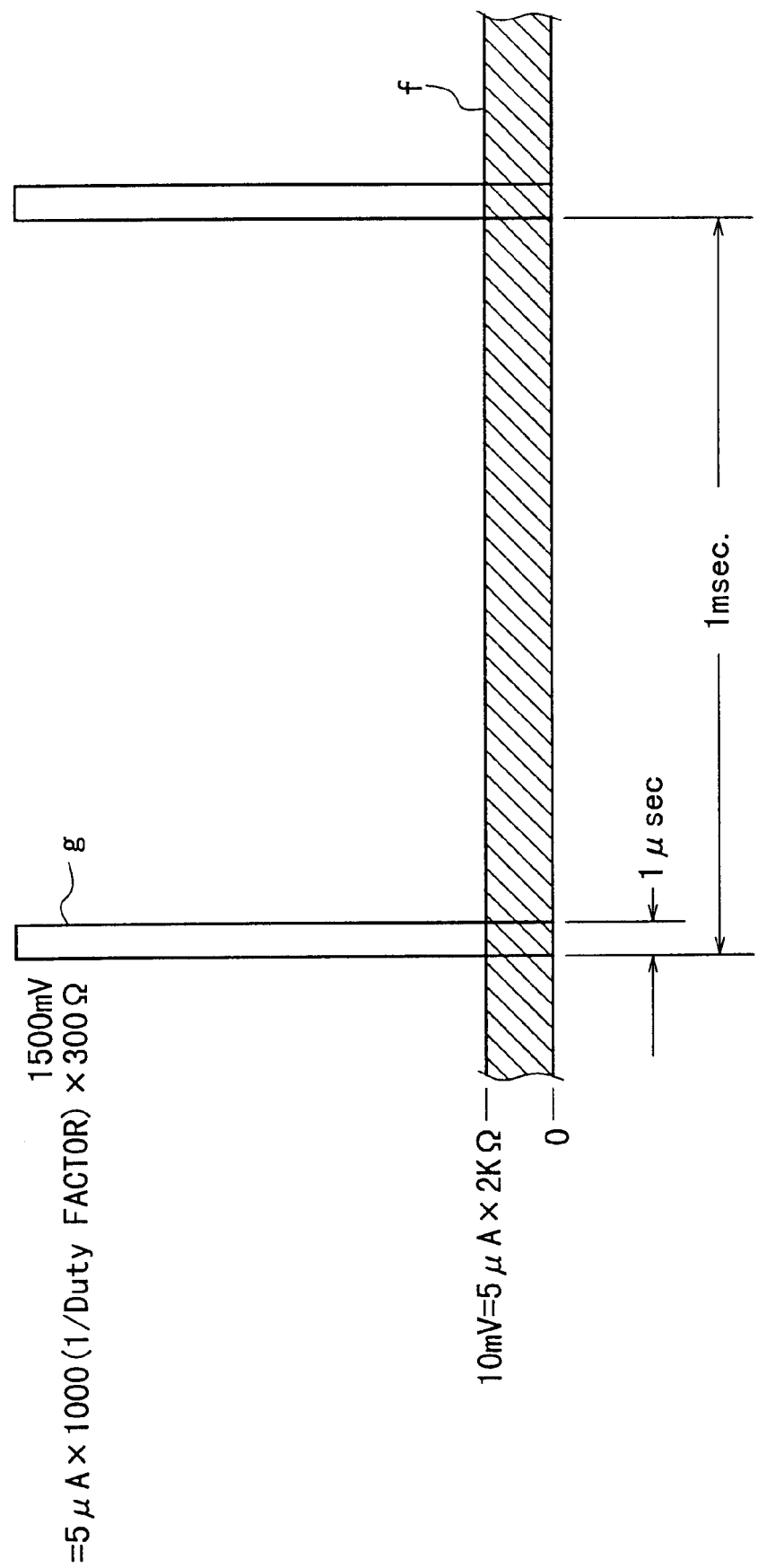
FIG. 13 shows waveforms illustrating a waveform of the pulse-shaped driving signal used for the gas sensor according to the third embodiment, together with a direct current voltage waveform.

In other words, the ON-OFF control effected by the driving circuit 14 for the output (the measured voltage signal Sv) from the amplifying circuit 110 allows the output from the driving circuit 114 to be the pulse-shaped driving signal Svp (the voltage signal) which has a crest value based on the electromotive force V2 during the period corresponding to the pulse width of the pulse signal Sp from the rectangular wave-generating circuit 112 and which has a crest value of, for example 0 μA during the other periods (see a waveform "g" shown in FIG. 13). The current iv, which corresponds to the driving signal Svp, is supplied to the outer pumping electrode 30. Since the pulse signal Sp outputted from the rectangular wave-generating circuit 112 has the frequency of 1 kHz, the frequency of the driving signal Svp is fixed to be the same frequency of 1 kHz.

Figure 12:
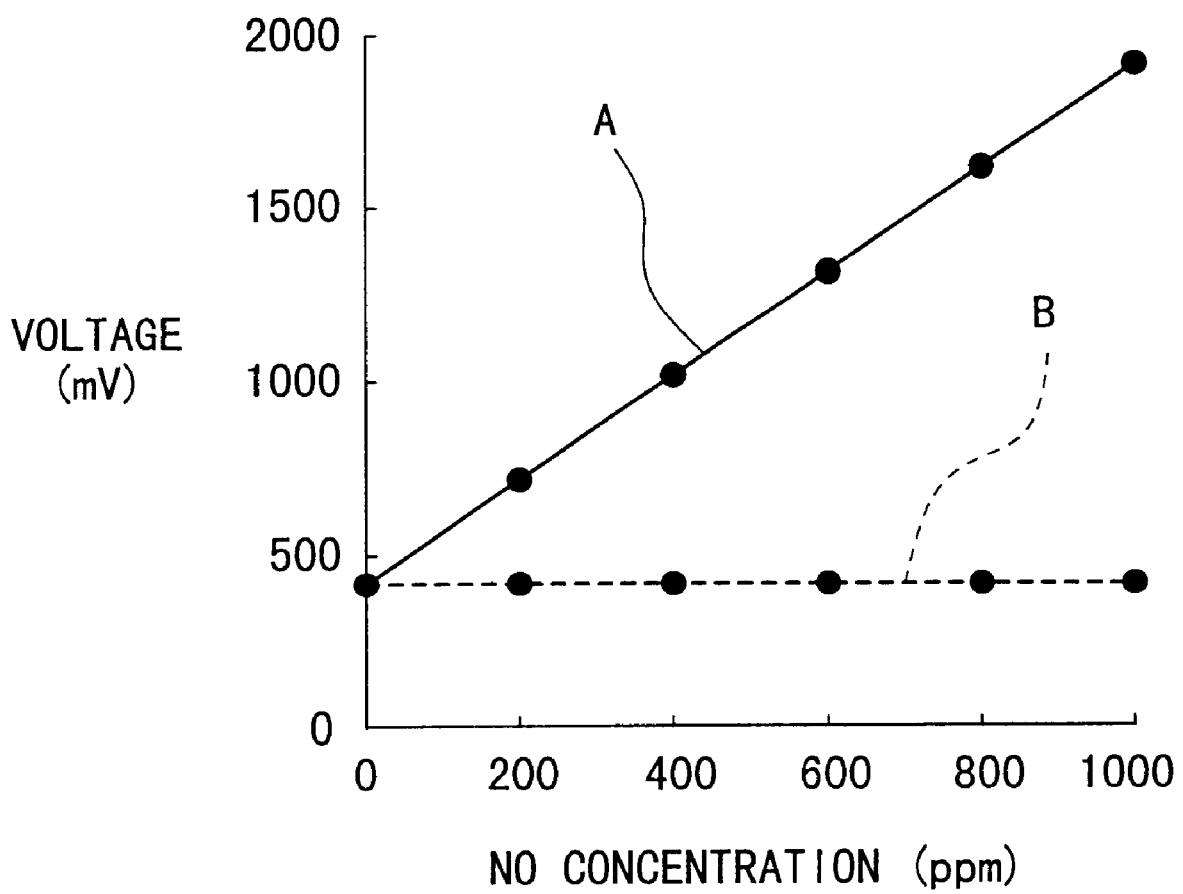
FIG. 12 shows a characteristic curve illustrating the change in voltage of a pulse-shaped driving signal with respect to the change in NO concentration concerning the gas sensor according to the third embodiment.

A characteristic shown in FIG. 12 represents a relationship between the NO concentration and the crest value (the voltage Vi obtained after conversion of the current iv into the voltage) of the current iv concerning the gas sensor according to the third embodiment (see a solid line A). According to the characteristic, it is understood that the crest value (the voltage Vi) of the current iv is linearly increased in response to the NO concentration, making it possible to measure the NO concentration.

As for the measuring system 64, for example, two types of circuits are conceived in the third embodiment as well. The first measuring system 64a comprises a voltage-detecting circuit 116 for detecting the voltage Vi (the voltage corresponding to the crest value of the current iv) extracted by the current-detecting resistor R2 to output its peak value and its average value, and an output circuit 118 for converting the output (the peak value and the average value) from the voltage-detecting circuit 116 on the basis of, for example, the characteristic shown in FIG. 12 into the NO concentration so that the concentration value is displayed, for example, by digital expression. The second measuring system 64b comprises an output circuit 120 for converting the measured voltage signal Sv supplied from the amplifying circuit 110 into the NO concentration so that the concentration value is displayed, for example, by digital expression.

The gas sensor 10C according to the third embodiment is basically constructed as described above. Next, its operation and effect will be explained.

At first, the electromotive force V2 between the reference electrode 38 and the detecting electrode 60 of the gas sensor 10C is measured by the electromotive force-measuring circuit 70. The electromotive force V2 is compared with the comparing voltage Vb in the comparing circuit 74. The comparing circuit 74 outputs, as the voltage signal Sa, the difference between the electromotive force V2 and the comparing voltage Vb. The voltage signal Sa is amplified with the predetermined gain (for example, 500 times) to give the measured voltage signal Sv by the aid of the amplifying circuit 110 disposed at the downstream stage.

The measured voltage signal Sv is introduced into the driving circuit 114. The driving circuit 114 performs the ON-OFF control for the inputted measured voltage signal Sv on the basis of the pulse signal Sp supplied from the rectangular wave-generating circuit 112. Accordingly, the pulse-shaped driving signal Svp (the voltage signal) is obtained, which has the voltage level based on the value of the electromotive force V2. The current iv corresponding to the driving signal Svp is supplied to the outer pumping electrode 30. During this process, the current iv, which is determined by the voltage of the driving signal Svp and the impedance between the outer pumping electrode 30 and the detecting electrode 60, flows between the outer pumping electrode 30 and the detecting electrode 60 during the period corresponding to the pulse width of the driving signal Svp. That is, the pulse-shaped current iv flows between the outer pumping electrode 30 and the detecting electrode 60.

The voltage Vi (the crest value of the current iv), which is extracted by the current-detecting resistor R2, is detected by the voltage-detecting circuit 116 of the first measuring system 64a to make output as the peak value or the average value thereof. The peak value or the average value is converted into the NOx concentration by the output circuit 118 disposed at the downstream stage, and the concentration is displayed, for example, by digital expression. In the second measuring system 64b, the measured voltage signal Sv from the amplifying circuit 110 is converted into the NOx concentration by the output circuit 120, and the concentration is displayed, for example, by digital expression.

As described above, in the gas sensor 10C according to the third embodiment, the pulse-shaped current iv, the crest value of which is controlled on the basis of the electromotive force V2 generated between the detecting electrode 60 and the reference electrode 38, is supplied to the outer pumping electrode 30. Therefore, the following effect can be obtained.

In the case of the conventional measuring method, for example, as shown by a broken line B in the characteristic curve shown in FIG. 12, the detection can be performed by merely using the small change in which the voltage (the pumping voltage) between the reference electrode 38 and the detecting electrode 60 is 450 mV to 460 mV (the increment corresponding to the direct current impedance between the reference electrode 38 and the detecting electrode 60, i.e., 10 k$\Omega$×5 $\mu$A=10 mV) with respect to, for example, the change in concentration of 0 to 1000 ppm. On the contrary, in the case of the gas sensor 10C according to the third embodiment, as shown by the solid line A in the characteristic curve shown in FIG. 12, the large change is obtained (the increment corresponding to the alternating current impedance between the outer pumping electrode 30 and the detecting electrode 60, i.e., 300 $\Omega$×5000 $\mu$A=1500 mV). Therefore, the system is scarcely affected by the noise, and it is possible to accurately measure the NOx concentration.

Next, a specified example of the gas sensor 10C according to the third embodiment described above will be explained while making comparison with a case in which a direct current is supplied to the reference electrode 38. This description is illustrative of a case in which comparison is made by using the voltage Vi obtained after conversion into the voltage for the current iv supplied to the reference electrode 38.

At first, when the direct current is allowed to flow, a waveform "f" as shown in FIG. 13 is obtained. That is, the electromotive force of 450 mV+the amount of voltage drop based on the direct current impedance between the reference electrode 38 and the detecting electrode 60 and the pumping current flowing between the reference electrode 38 and the detecting electrode 60 of 2 k$\Omega$×5 $\mu$A (1000 ppm)=450 mV+10 mV. Of this voltage, the voltage of 10 mV except for the amount of the electromotive force is a voltage which is substantially used for the oxygen pumping.

Assuming that there is given one cycle=1 msec for the pulse signal Sp outputted from the rectangular wave-generating circuit 112, the quantity of electricity is 5 $\mu$A×1 msec=5×10$^{-3}$ $\mu$A·sec=5×10$^{-3}$$\mu$ coulombs (corresponding to the amount of oxygen subjected to the pumping) when the direct current flows.

On the other hand, in the gas sensor 10C according to the third embodiment, the current iv, which corresponds to the pulse-shaped driving signal Svp having a quantity of electricity equivalent to the quantity of electricity (5×10$^{-3}$$\mu$ coulombs), is supplied to the outer pumping electrode 30. Simultaneously, for example, the voltage-detecting circuit 116 is used to measure the crest value (the peak value or the average value) of the current iv after conversion into the voltage. That is, the crest value of the current iv is controlled so as to provide the same value as the direct current value after the conversion into the voltage for the direct current (10 mV)×unit time (1 msec).

In the case of the specified example described above, the quantity of electricity, which is equivalent of the quantity of electricity of 5×10$^{-3}$ $\mu$A·sec, is (V/R)×1 $\mu$sec. R represents the internal resistance between the outer pumping electrode 30 and the detecting electrode 60. R is greatly different from the value of 2 k$\Omega$ obtained for the direct current, and it is 300 $\Omega$ as the alternating current impedance. Therefore, the quantity of electricity is (V/300)×1 $\mu$sec.

V is determined so that the quantity of electricity is equal to 5×10$^{-3}$ $\mu$A·sec. Accordingly, there is given V=5×10$^{-3}$ $\mu$A·sec/(1/300)×1 $\mu$sec=1500 mA·$\Omega$=1500 mV.

Therefore, when the pulse-shaped driving signal (the voltage signal) Svp having the frequency of 1 kHz, the pulse width of 1 $\mu$sec, and the crest value of 1500 mV is outputted from the driving circuit 114, then it is possible to perform the aimed pumping operation (the pumping operation for making the partial pressure of oxygen in the second chamber 26 to be the partial pressure of oxygen corresponding to the comparing voltage Vb). Simultaneously, it is possible to measure the NO concentration highly accurately without being affected by the electric noise.

Next, a modified embodiment (10Ca) of the gas sensor 10C according to the third embodiment will be explained with reference to FIG. 14. Components or parts corresponding to those shown in FIG. 11 are designated by the same reference numerals.

Figure 14:
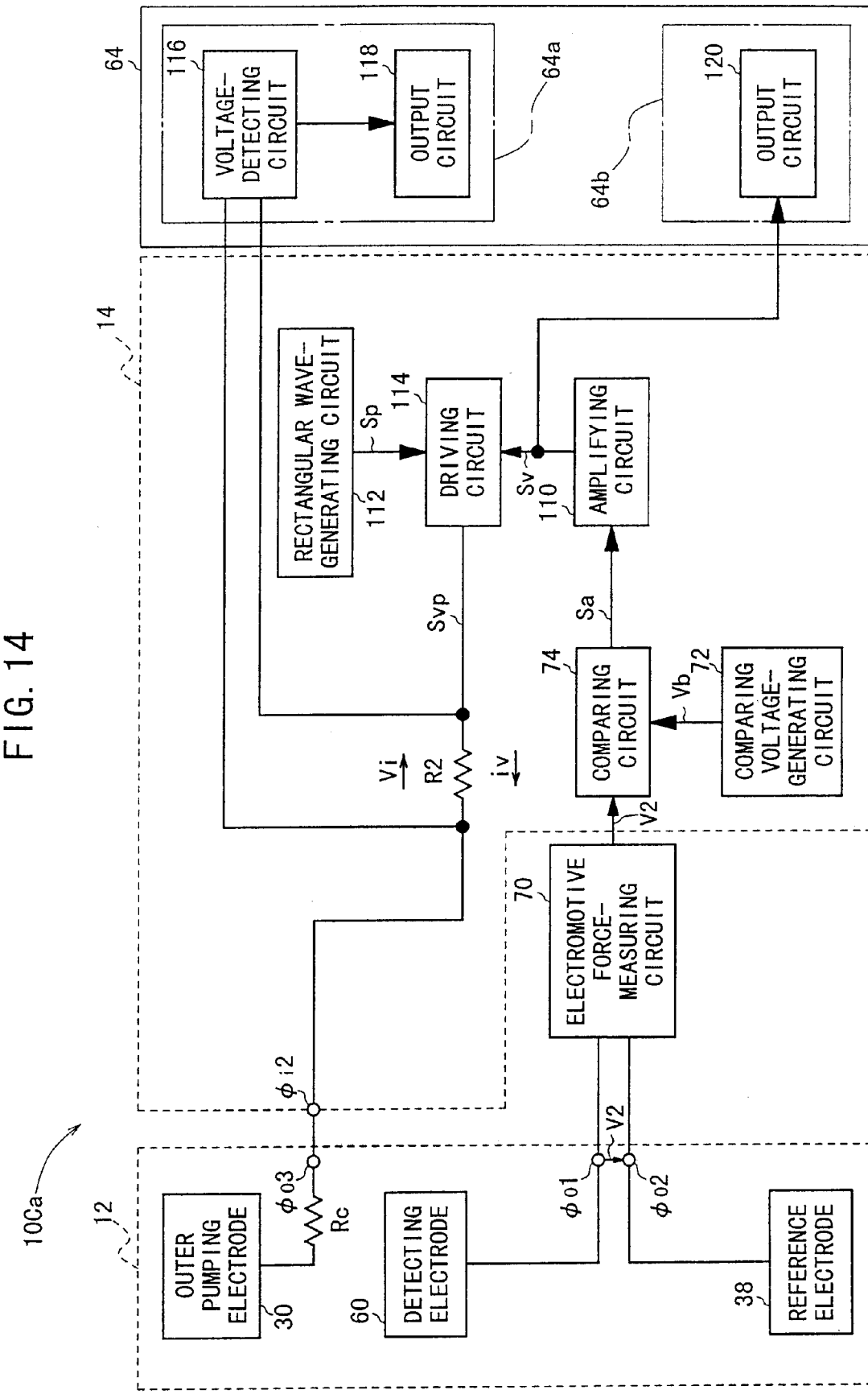
FIG. 14 shows a block diagram illustrating a circuit system of a gas sensor according to a modified embodiment of the third embodiment.

As shown in FIG. 14, the gas sensor 10Ca according to the modified embodiment is constructed in approximately the same manner as in the gas sensor 10C according to the third embodiment described above (see FIG. 11). However, the former is different from the latter in that an adjusting resistor Rc is connected in series to the current supply line from the current supply circuit 14 to the outer pumping electrode 30. In the illustrated embodiment, the adjusting resistor Rc is connected between the outer pumping electrode 30 and the second external output terminal φo2 of the main sensor device 12.

According to the gas sensor 10Ca concerning the modified embodiment, the following effects are obtained. That is, the relationship between the NOx concentration and the voltage of the driving signal Svp can be maintained to be constant by adjusting the size of the adjusting resistor Rc in conformity with the dispersion among individuals concerning the limiting current value of the main sensor device 12. Moreover, it is possible to further increase the change in voltage of the driving signal Svp with respect to the change in NOx concentration.

For example, it is assumed that the adjusting resistor Rc is 1 kΩ. In the case of the embodiment described above, the duty ratio of the driving signal Svp is 1/1000. Therefore, the pumping current iv, which flows between the outer pumping electrode 30 and the detecting electrode 60, is obtained by multiplying 5 µA by 1000. That is, the pulse-shaped current iv of 5 mA flows. The voltage drop of 5 V occurs in the adjusting resistor Rc. The voltage of the driving signal Svp is approximately 5 V+1.5 V (the voltage drop caused by the internal resistance between the reference electrode 38 and the detecting electrode 60)+450 mV (the electromotive force)=6.95 V.

The voltage is 450 mV when the NOx concentration is 0 ppm, while a large change of 6.5 V can be used for the detection for the change of the NOx concentration of 0 to 1000 ppm. The following assumption holds for the dispersion among individuals concerning the limiting current value of the main sensor device 12. That is, for example, it is assumed that the measurement is performed by supplying a direct current to a main sensor device 12 having a large limiting current. For example, there is given the adjusting resistor Rc=(6.5 V−300 Ω×7 mA)/7 mA=(4.4×1000/7)=629 Ω for a main sensor device 12 in which a direct current of 7 µA is allowed to flow for a NOx concentration of 1000 ppm. Thus, it is possible to allow the voltage at 1000 ppm to be 6.5 V+450 mV=6.95 V.

As described above, the change in voltage Vi (i.e., the change in crest value of the current iv) with respect to the NOx concentration is the high voltage change which is 100 times that measured by using the direct current, by supplying, to the outer pumping electrode 30, the current iv corresponding to the pulse-shaped driving signal Svp outputted from the driving circuit 114. Thus, it is possible to obtain the effect that the system is scarcely affected by the electric noise. Additionally, it is possible to effectively compensate the dispersion among individual main sensor devices 12.

In the gas sensors 10A to 10C according to the fist to third embodiments described above (including the respective modified embodiments), the pulse shape of the pulse signal outputted from the rectangular wave-generating circuit 76, 112 is the rectangular wave. Besides, it is allowable to use any waveform including, for example, trapezoidal waves, triangular waves, and sinusoidal waves (half waves).

Preferably, the electromotive force-measuring circuit 70 is provided with a smoothing circuit. In this embodiment, the smoothing circuit preferably has a time constant τ which is not less than 10 times the pulse cycle of the pulse signal outputted from the rectangular wave-generating circuit 76, 112.

As for the lower limit value of the frequency of the pulse signal outputted from the rectangular wave-generating circuit 76, 112, it is preferable to provide a cycle of about 1/10 fold of the response performance required for the gas sensors 10A to 10C (including the respective modified embodiments). For example, when the requirement for the response performance of the gas sensors 10A to 10C (including the respective modified embodiments) is 100 msec, it is preferable to use a pulse signal having a cycle of 10 msec, i.e., not less than 100 Hz. Thus, it is possible to sufficiently smooth the electromotive force V2 by using the smoothing circuit without deteriorating the response performance.

In the gas sensor 10A according to the first embodiment (including the modified embodiment), it is preferable that the pulse width of the rectangular wave signal Sf outputted from the rectangular wave-generating circuit 76 is decreased as short as possible, because it is possible to set a high crest value for the constant current i.

Also in the gas sensor 10B according to the second embodiment (including the modified embodiment), it is preferable that the pulse width Pw of the rectangular wave signal Sd outputted from the rectangular wave-generating circuit 76 is decreased as short as possible, because it is possible to set a high crest value for the constant current i.

In the gas sensor 10C according to the third embodiment, when the dispersion among individual main sensor devices 12 is not corrected without providing the adjusting resistor Rc, it is preferable that the frequency of the pulse signal Sp outputted from the rectangular wave-generating circuit 112 is low, because of the following reason. That is, the lower the frequency is, the higher the alternating current impedance is. Accordingly, the voltage change of the driving signal Svp is increased.

In the modified embodiment 10Ca of the gas sensor according to the third embodiment, the dispersion among individual main sensor devices 12 is corrected by providing the adjusting resistor Rc. Therefore, it is preferable that the frequency of the pulse signal Sp outputted from the rectangular wave-generating circuit 112 is high, because of the following reason. That is, the higher the frequency is, the lower the alternating current impedance is. Accordingly, the change in pumping current, which is determined by the value of the adjusting resistor Rc, is scarcely affected by the change in impedance of the measuring pumping cell which depends on, for example, the change in temperature and the change in durability.

The gas sensors 10A to 10C according to the first to third embodiments described above (including the respective modified embodiments) are illustrative of the case in which the NOx concentration in the measurement gas is measured. However, the present invention is also applicable, for example, to oxygen sensors, inflammable gas sensors, $CO_2$ sensors, and H₂O sensors based on the use of the oxygen pump. The present invention is also applicable to H₂ sensors and H₂O sensors based on the use of the proton ion-conductive member, as well as to controlling pumps for controlling the concentration of such specified gases.

It is a matter of course that the gas sensor and the method for controlling the gas sensor according to the present invention are not limited to the embodiments described above, which may be embodied in other various forms.

As explained above, according to the gas sensor and the method for controlling the gas sensor concerning the present invention, it is possible to highly accurately measure a predetermined gas component while scarcely being affected by the electric noise or the like.

Further, it is possible to compensate the dispersion among individual sensors without increasing the number of terminals, which is advantageous in view of the production cost.

What is claimed is:

1. A gas sensor comprising:
    a main pumping means for pumping-processing oxygen contained in a measurement gas introduced from an external space, comprising a solid electrolyte contacting with said external space, and an inner pumping electrode and an outer pumping electrode formed on inner and outer surfaces of said solid electrolyte; and
    a measuring pumping means for decomposing a predetermined gas component contained in said measurement gas after being pumping-processed by said main pumping means by the aid of a catalytic action and/or electrolysis, and pumping-processing oxygen produced by said decomposition via said outer pumping electrode of said main pumping means, wherein:
        a concentration of oxygen is controlled and/or the predetermined gas component is measured by allowing a pulse-shaped current to flow through said measuring pumping means;
        the gas sensor further comprising:
            an electromotive force-measuring circuit for constantly measuring the electromotive force corresponding to a difference between an amount of oxygen produced by said decomposition of said predetermined gas component and an amount of oxygen contained in a reference gas;
            a duty ratio control means for controlling a duty ratio of said pulse-shaped current corresponding to a difference between an the electromotive force measured by said electromotive force-measuring circuit and a comparing voltage; and
            a measuring circuit for at least converting the duty ratio of the pulse-shaped current into a concentration of said predetermined gas component.

2. The gas sensor according to claim 1, wherein a resistor is connected in series to a supply line of said pulse-shaped current to said measuring pumping means.

3. The gas sensor according to claim 2, wherein said resistor is selected or adjusted depending on performance of a sensor element.

4. The gas sensor according to claim 1, wherein said predetermined gas component is NOx.

5. A method for controlling a gas sensor, the gas sensor comprising:
    a main pumping means for pumping-processing oxygen contained in a measurement gas introduced from an external space, comprising a solid electrolyte contacting with said external space, and an inner pumping electrode and an outer pumping electrode formed on inner and outer surfaces of said solid electrolyte; and
    a measuring pumping means for decomposing a predetermined gas component contained in said measurement gas after being pumping-processed by said main pumping means by the aid of a catalytic action and/or electrolysis, and pumping-processing oxygen produced by said decomposition via said outer pumping electrode of said main pumping means;
    wherein a concentration of oxygen is controlled and/or the predetermined gas component is measured by allowing a pulse-shaped current to flow through said measuring pumping means;
    wherein the method for controlling the gas sensor comprises the steps of:
        measuring constantly the electromotive force corresponding to a difference between an amount of oxygen produced by said decomposition of said predetermined gas component and an amount of oxygen contained in a reference gas;
        controlling a duty ratio of said pulse-shaped current corresponding to a difference between an the electromotive force measured by said electromotive force-measuring circuit and a comparing voltage; and
        converting at least the duty ratio of the pulse-shaped current into a concentration of said predetermined gas component.

6. The method for controlling said gas sensor according to claim 5, wherein said predetermined gas component is NOx.

* * * * *

UNITED STATES PATENT AND TRADEMARK OFFICE
CERTIFICATE OF CORRECTION

PATENT NO.   : 6,623,618 B1
DATED        : September 23, 2003
INVENTOR(S)  : Nobuhide Kato, Yasuhiko Hamada and Nobuyuki Kokune It is certified that error appears in the above-identified patent and that said Letters Patent is hereby corrected as shown below:

<u>Column 10,</u>
Line 15, please change "affects" to -- affect --.

<u>Column 25,</u>
Lines 21 and 27, please delete "a";
Line 24, please delete "with";
Line 47, please delete "an".

<u>Column 26,</u>
Lines 14 and 20, please delete "a";
Line 17, please delete "with".

Signed and Sealed this

Twenty-third Day of December, 2003

JAMES E. ROGAN
*Director of the United States Patent and Trademark Office*